US012059549B2

(12) United States Patent
Müller et al.

(10) Patent No.: US 12,059,549 B2
(45) Date of Patent: Aug. 13, 2024

(54) DRUG DELIVERY DEVICE

(71) Applicant: SENSILE MEDICAL AG, Olten (CH)

(72) Inventors: Matthias Müller, Hägendorf (CH);
Christian Huber, Bern (CH); Fabian
Bürli, Stüsslingen (CH); Alexandre
Perrier, Liestal (CH)

(73) Assignee: SENSILE MEDICAL AG, Olten (CH)

( * ) Notice: Subject to any disclaimer, the term of this
patent is extended or adjusted under 35
U.S.C. 154(b) by 0 days.

(21) Appl. No.: 18/282,248

(22) PCT Filed: Mar. 8, 2022

(86) PCT No.: PCT/EP2022/055835
§ 371 (c)(1),
(2) Date: Sep. 15, 2023

(87) PCT Pub. No.: WO2022/194611
PCT Pub. Date: Sep. 22, 2022

(65) Prior Publication Data
US 2024/0033423 A1 Feb. 1, 2024

(30) Foreign Application Priority Data
Mar. 15, 2021 (EP) ..................................... 21162675

(51) Int. Cl.
A61M 5/145 (2006.01)
A61M 5/14 (2006.01)
A61M 5/142 (2006.01)
(52) U.S. Cl.
CPC ...... *A61M 5/14526* (2013.01); *A61M 5/1413*
(2013.01); *A61M 5/14248* (2013.01);
(Continued)

(58) Field of Classification Search
CPC ............ A61M 5/14526; A61M 5/1413; A61M
5/14248; A61M 5/1456;
(Continued)

(56) References Cited

U.S. PATENT DOCUMENTS 5,769,824 A * 6/1998 Hjertman .......... A61M 5/14526
604/91
7,726,955 B2 6/2010 Ryser et al.
(Continued)

FOREIGN PATENT DOCUMENTS

JP 2015-80473 4/2015
WO WO 2007/074363 7/2007
(Continued)

OTHER PUBLICATIONS

Written Opinion in International Application No. PCT/EP2022/
055835, May 17, 2022, pp. 1-7.
(Continued)

Primary Examiner — James D Ponton
(74) Attorney, Agent, or Firm — SALIWANCHIK,
LLOYD & EISENSCHENK

(57) ABSTRACT

A drug delivery device (1) having a delivery unit (3)
including a drug container (6), a liquid flow system (7), a
pumping system (8), and a casing (9) enclosing therein the
drug container, the pumping system and at least a part of the
liquid flow system is disclosed. The drug container has a
barrel portion (6a) and a plunger (12) slidably mounted
within the barrel portion and sealing the drug (78) within the
container at one end of the barrel portion. The drug container
is contained within a container receiving cavity (75) of a
container casing portion (38) and the container receiving
cavity is fluidically interconnected to a fluid outlet (31) of
the pumping system (8) in a gas tight manner. The pumping
system pumps environmental air into the container receiving
(Continued)

cavity (75) thus applying pressure on a back end (73) of the plunger for delivery of a liquid drug.

15 Claims, 23 Drawing Sheets

(52) U.S. Cl.
CPC ... *A61M 5/1456* (2013.01); *A61M 2005/1401* (2013.01); *A61M 2005/14252* (2013.01); *A61M 2005/14268* (2013.01); *A61M 2005/14573* (2013.01); *A61M 2202/0007* (2013.01); *A61M 2202/04* (2013.01); *A61M 2205/073* (2013.01); *A61M 2205/10* (2013.01); *A61M 2205/123* (2013.01); *A61M 2205/13* (2013.01); *A61M 2205/3306* (2013.01)

(58) Field of Classification Search
CPC .......... A61M 2005/1401; A61M 2005/14252; A61M 2005/14268; A61M 2005/14573; A61M 2202/0007; A61M 2202/04; A61M 2205/073; A61M 2205/10; A61M 2205/123; A61M 2205/13; A61M 2205/3306; A61M 5/14256; A61M 2005/14513

See application file for complete search history.

(56) References Cited

U.S. PATENT DOCUMENTS

| | | |
|---|---|---|
| 8,282,366 B2 | 10/2012 | Hilber et al. |
| 8,382,700 B2 | 2/2013 | Straessler et al. |
| 8,957,674 B2 | 2/2015 | Genoud et al. |
| 9,222,470 B2 | 12/2015 | Genoud et al. |
| 9,302,285 B2 | 4/2016 | Marbet et al. |
| 9,662,621 B2 | 5/2017 | Beyer et al. |
| 10,076,605 B2 | 9/2018 | Marbet et al. |
| 10,143,798 B2 | 12/2018 | Marbet et al. |
| 10,632,249 B2 | 4/2020 | Marbet et al. |
| 10,954,928 B2 | 3/2021 | Burli et al. |
| 11,009,018 B2 | 5/2021 | Wyss et al. |
| 11,009,026 B2 | 5/2021 | Girschweiler et al. |
| 11,022,107 B2 | 6/2021 | Brandt et al. |
| 11,160,922 B2 | 11/2021 | Just |
| 11,612,687 B2 | 3/2023 | Marbet |
| 11,744,940 B2 | 9/2023 | Wieser et al. |
| 2009/0030382 A1 | 1/2009 | Brandt et al. |
| 2010/0241063 A1 | 9/2010 | Straessler et al. |
| 2012/0046651 A1 | 2/2012 | Beyer et al. |
| 2014/0088506 A1 | 3/2014 | Heller et al. |
| 2014/0231549 A1 | 8/2014 | Thiemer et al. |
| 2018/0272059 A1 | 9/2018 | Marbet et al. |
| 2020/0198814 A1* | 6/2020 | Wegener .............. A61M 1/0281 |
| 2022/0031940 A1 | 2/2022 | Hulliger et al. |
| 2022/0273876 A1* | 9/2022 | Menz .................... A61M 5/155 |
| 2022/0323672 A1 | 10/2022 | Cassagne et al. |
| 2023/0398289 A1 | 12/2023 | Wieser et al. |
| 2024/0033422 A1 | 2/2024 | Büchi et al. |
| 2024/0066541 A1 | 2/2024 | Perrier et al. |

FOREIGN PATENT DOCUMENTS

| | | |
|---|---|---|
| WO | WO 2015/015379 | 2/2015 |
| WO | WO 2017/079136 | 5/2017 |
| WO | WO 2017/189174 | 11/2017 |
| WO | WO 2018/007251 | 1/2018 |
| WO | WO 2018/166699 | 9/2018 |
| WO | WO 2019/110455 | 6/2019 |
| WO | WO 2020/109409 | 6/2020 |
| WO | WO 2021/043614 | 3/2021 |
| WO | WO 2021/043843 | 3/2021 |

OTHER PUBLICATIONS

Claims as filed in U.S. Appl. No. 18/281,784, filed Sep. 13, 2023, pp. 1-4.
Claims as filed in U.S. Appl. No. 18/281,785, filed Sep. 13, 2023, pp. 1-4.
Claims as filed in U.S. Appl. No. 18/281,970, filed Sep. 14, 2023, pp. 1-4.
Claims as filed in U.S. Appl. No. 18/281,971, filed Sep. 14, 2023, pp. 1-3.
Claims as filed in U.S. Appl. No. 18/462,457, filed Sep. 7, 2023, pp. 1-3.
Claims as filed in U.S. Appl. No. 18/460,719, filed Sep. 5, 2023, pp. 1-3.
Claims as filed in U.S. Appl. No. 18/460,722, filed Sep. 5, 2023, pp. 1-3.
Claims as filed in U.S. Appl. No. 18/489,887, filed Oct. 19, 2023, pp. 1-3.
Claims as filed in U.S. Appl. No. 18/389,242, filed Nov. 14, 2023, pp. 1-3.

* cited by examiner

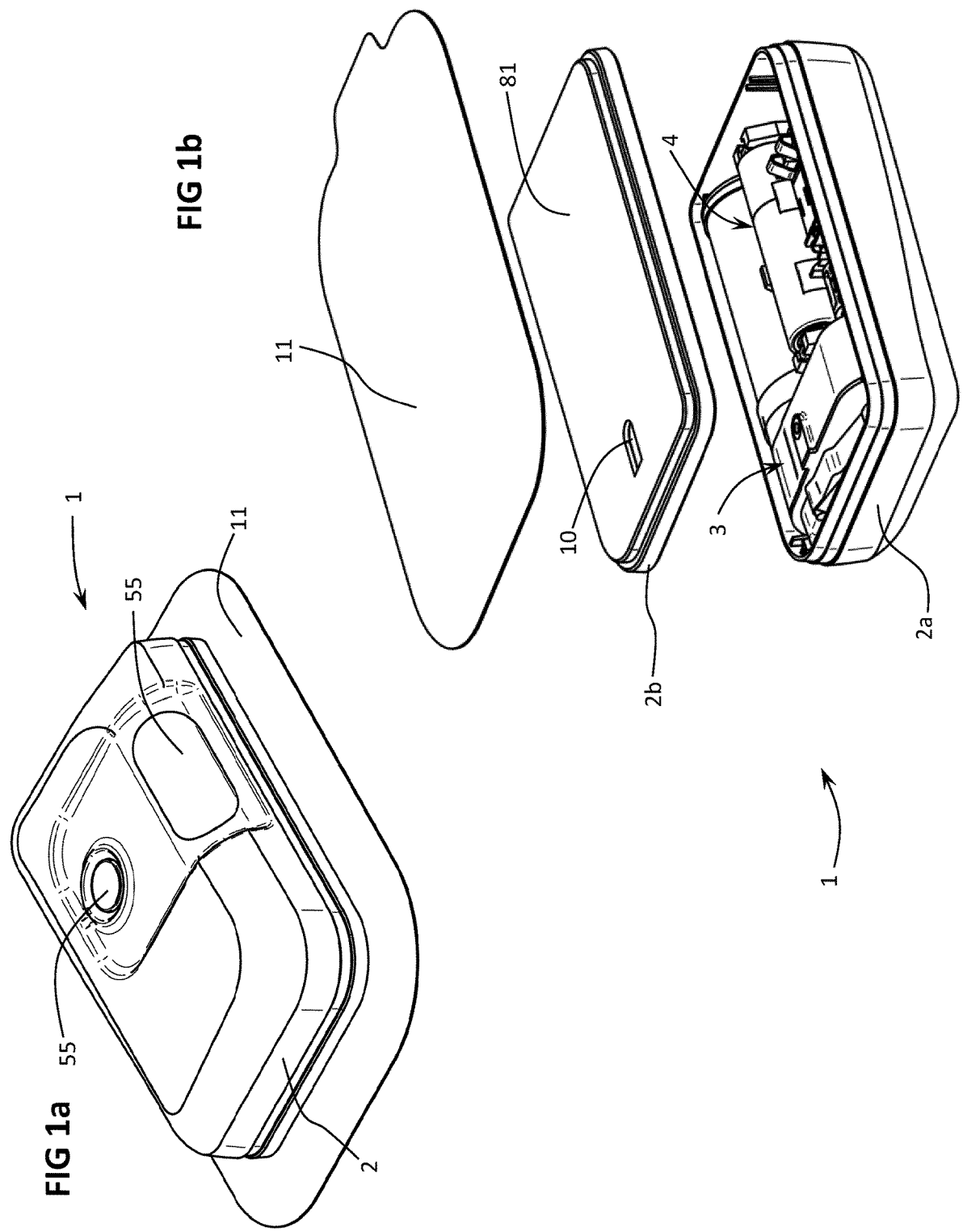

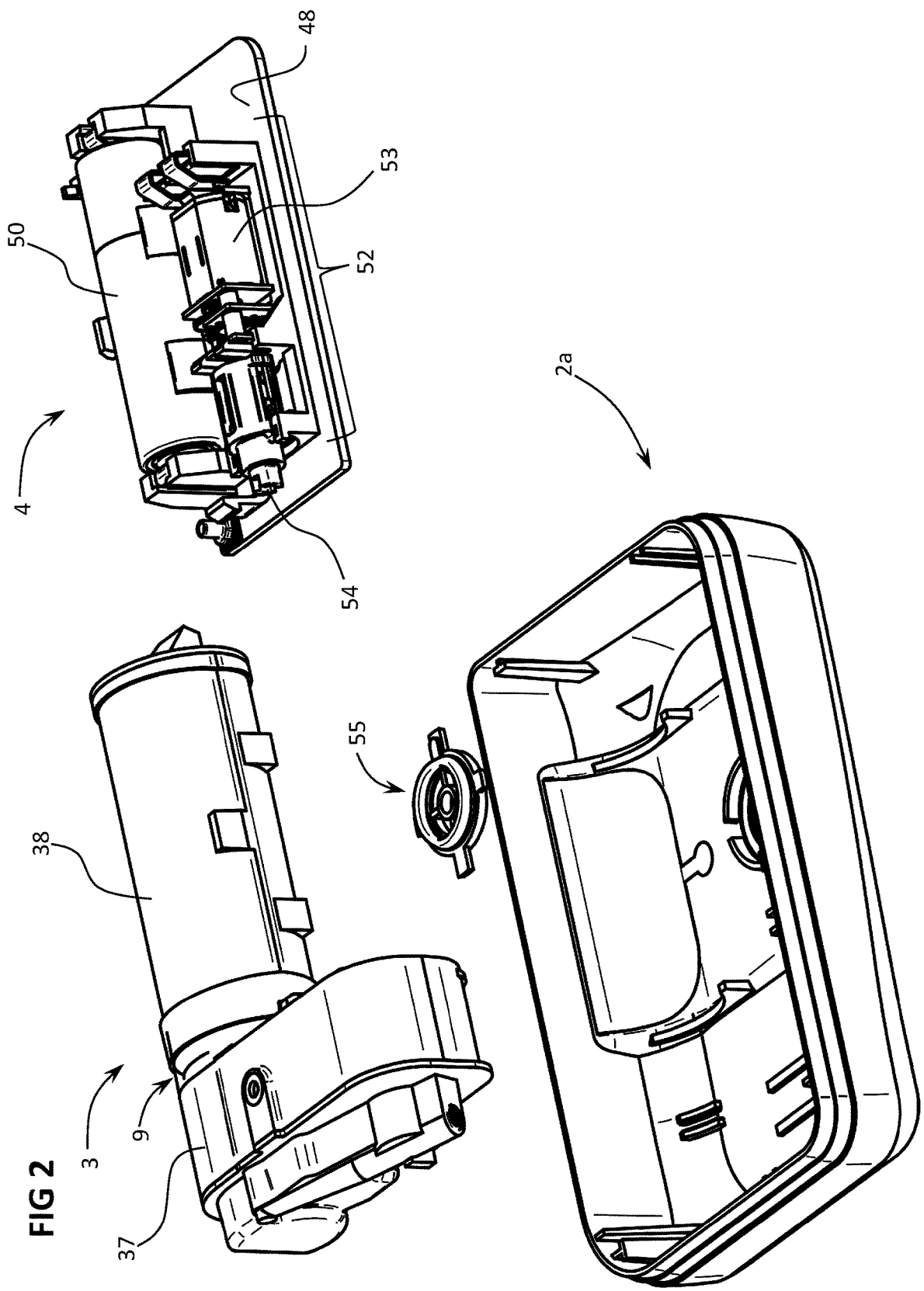

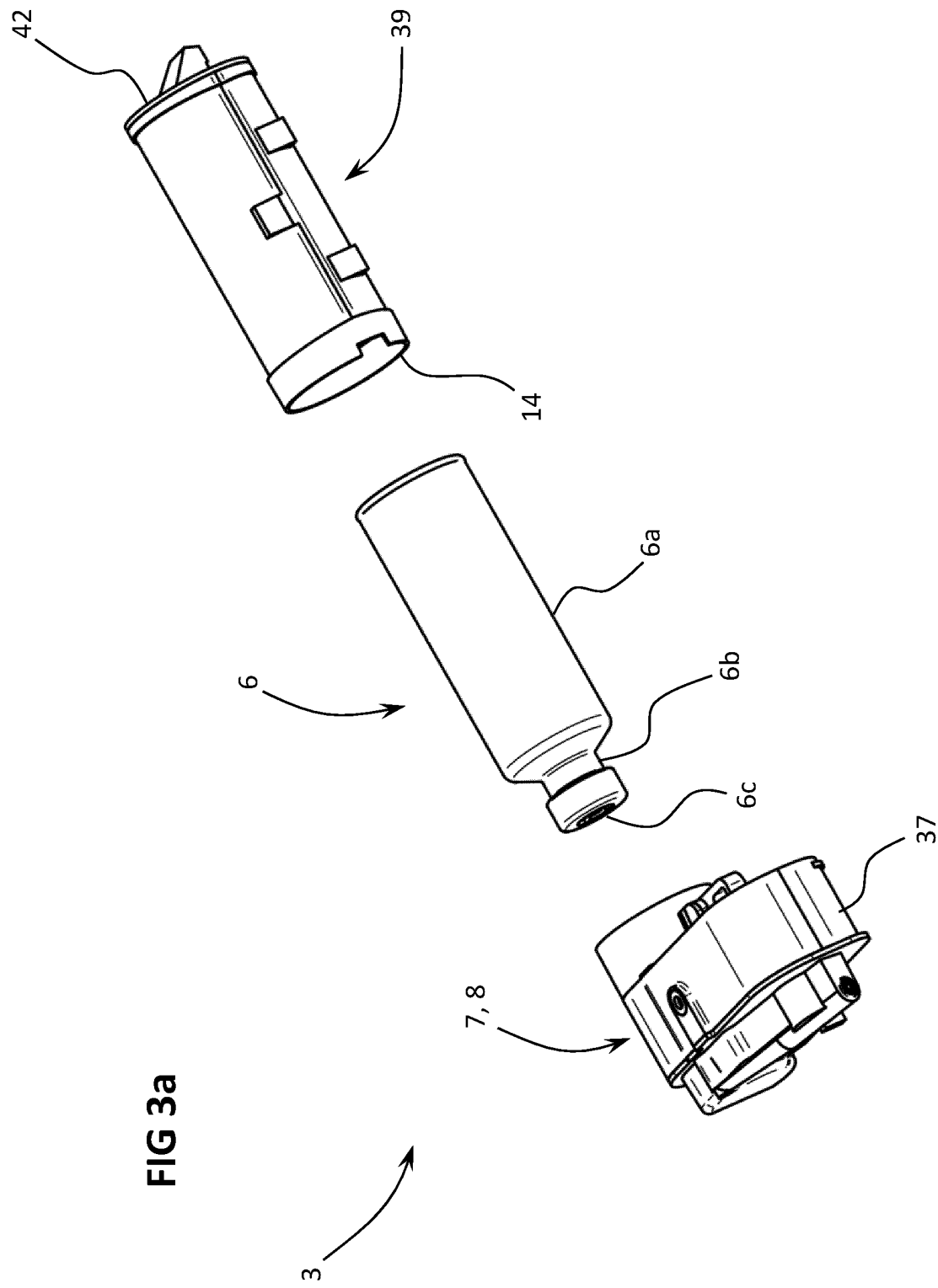

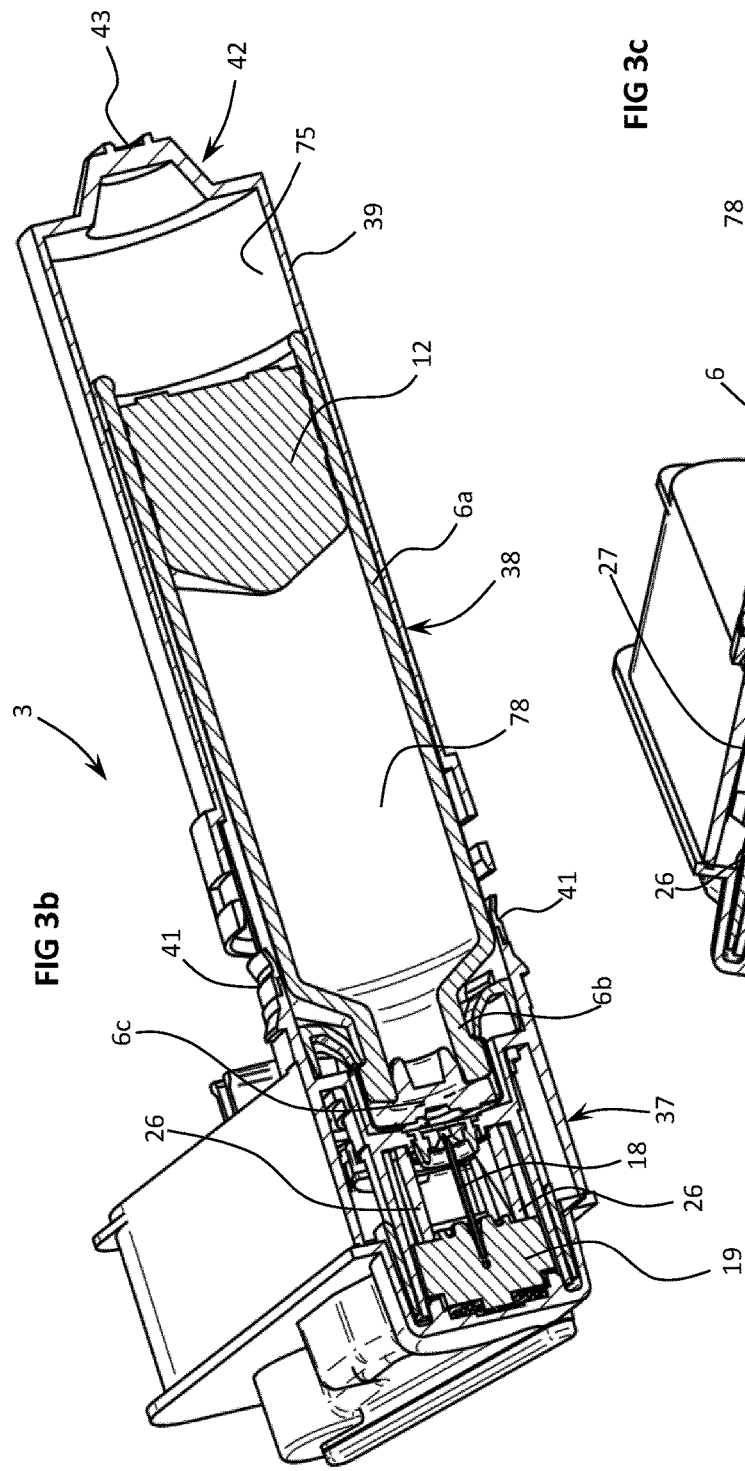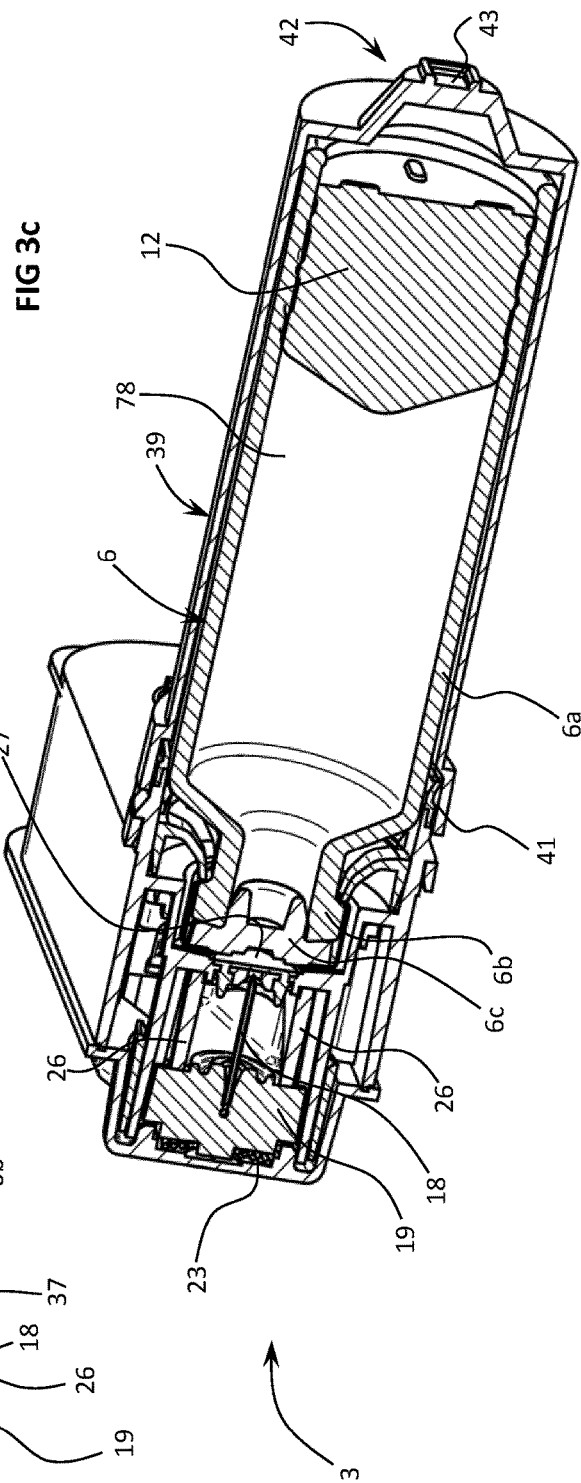

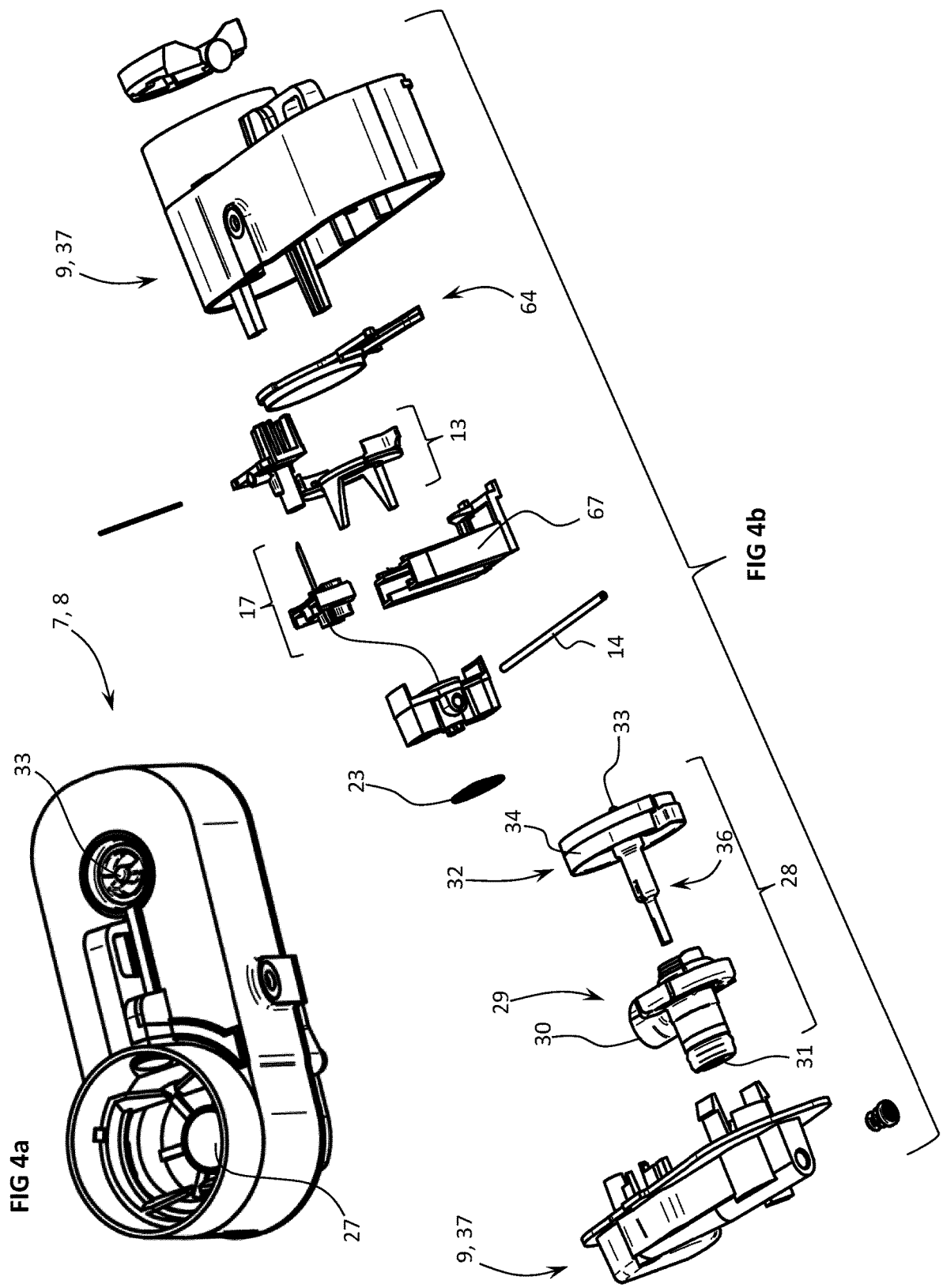

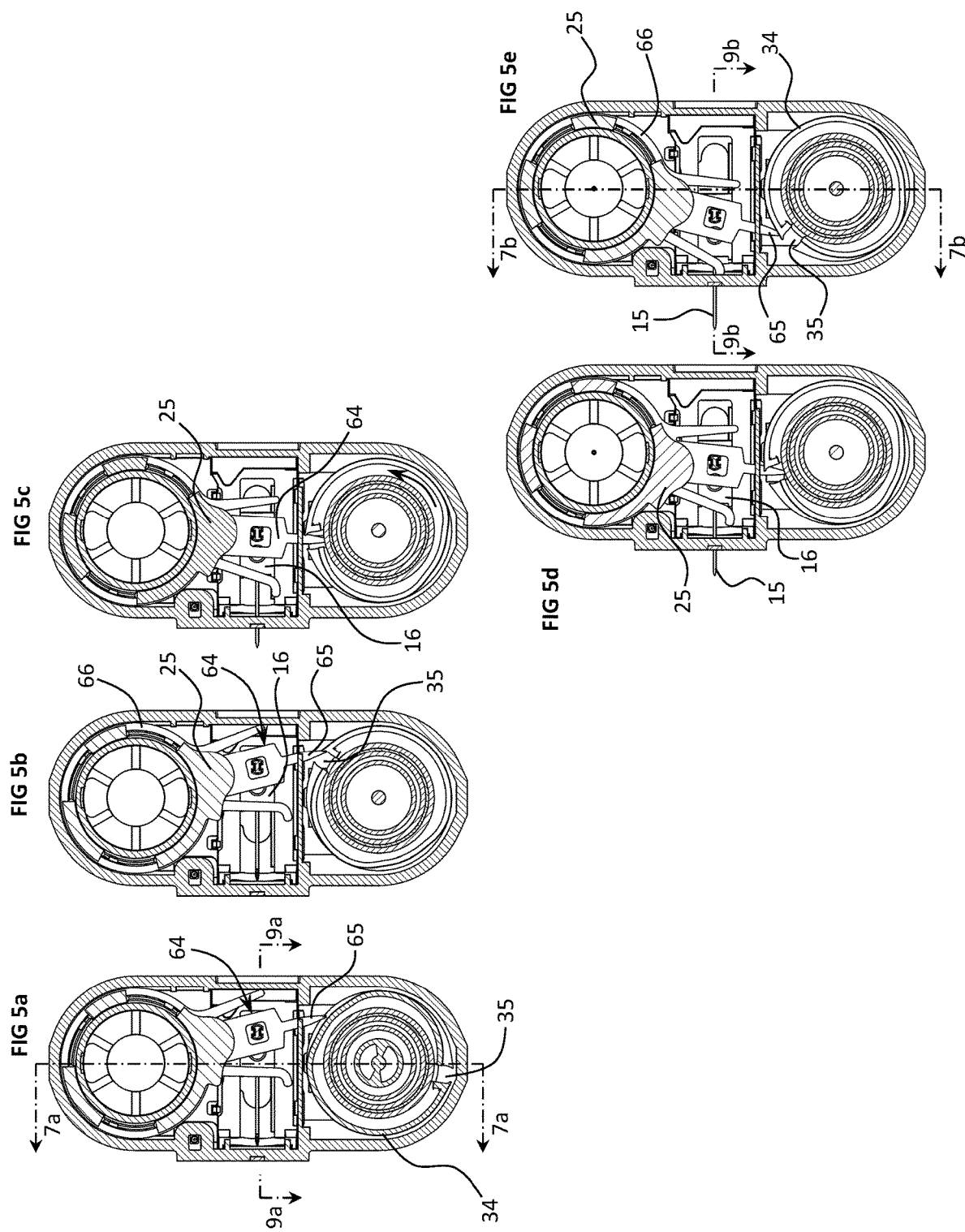

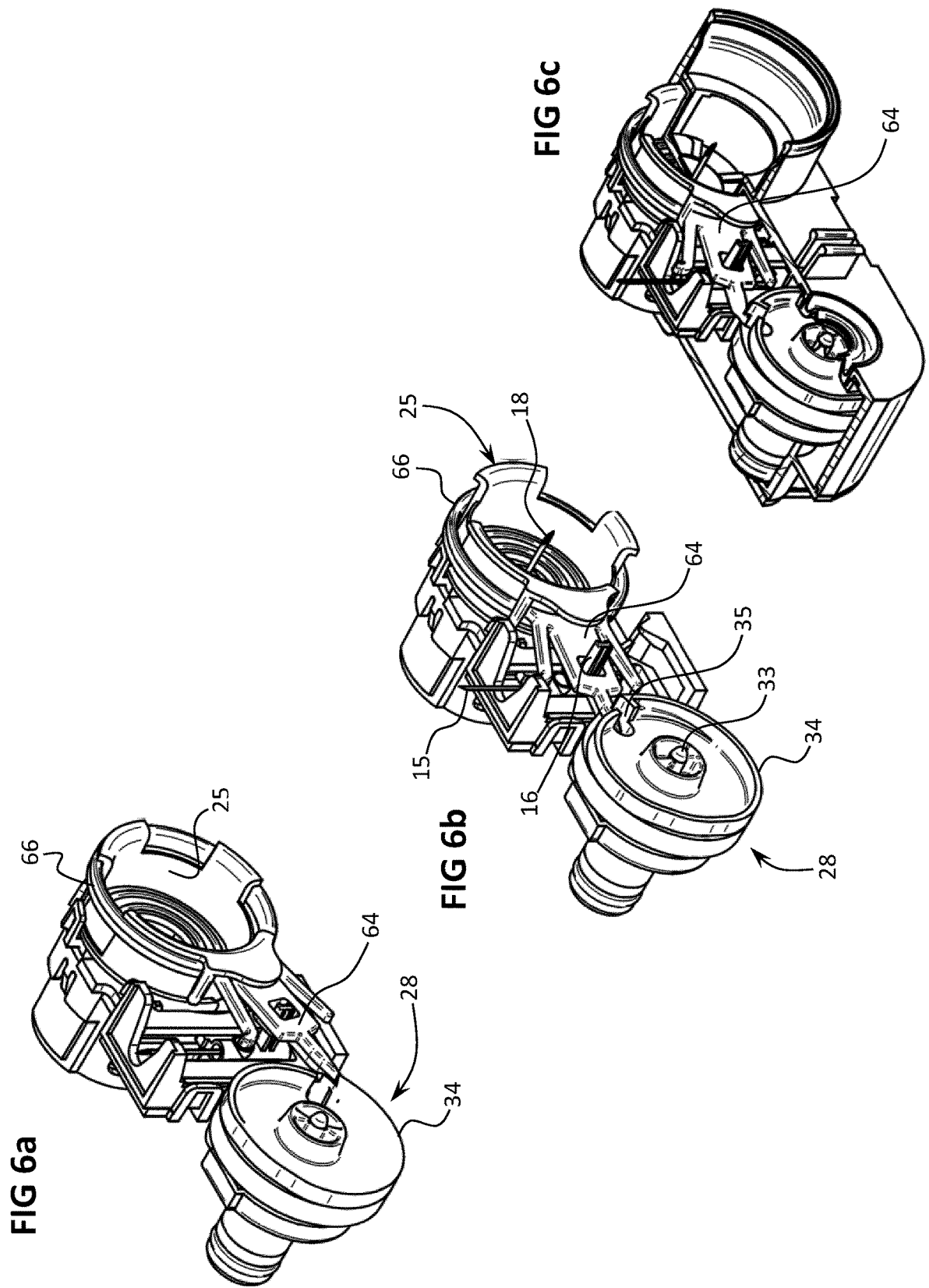

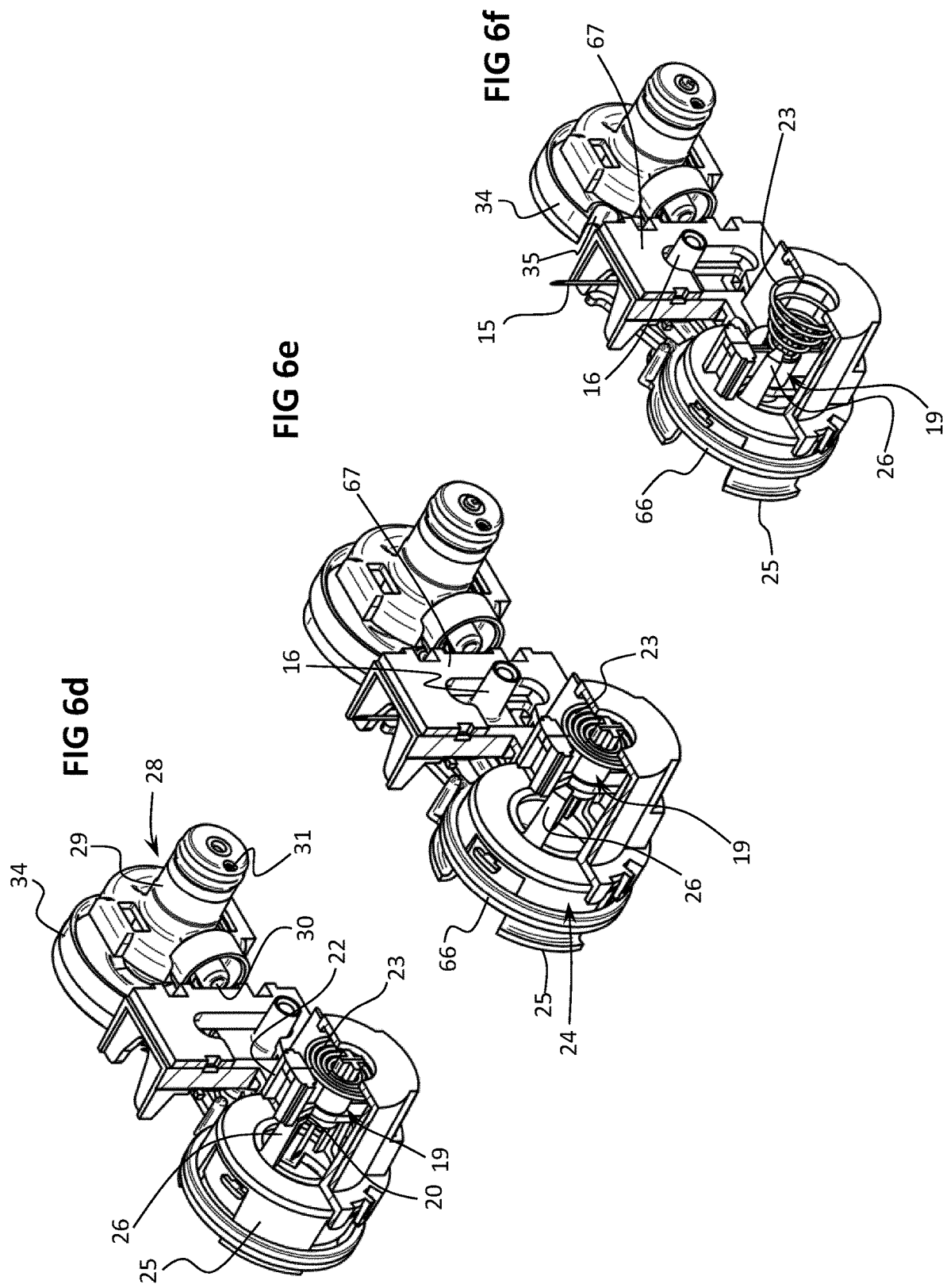

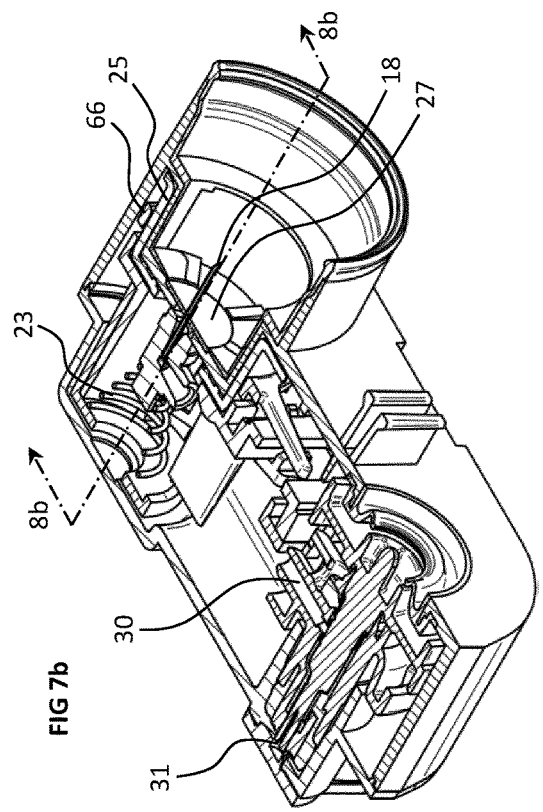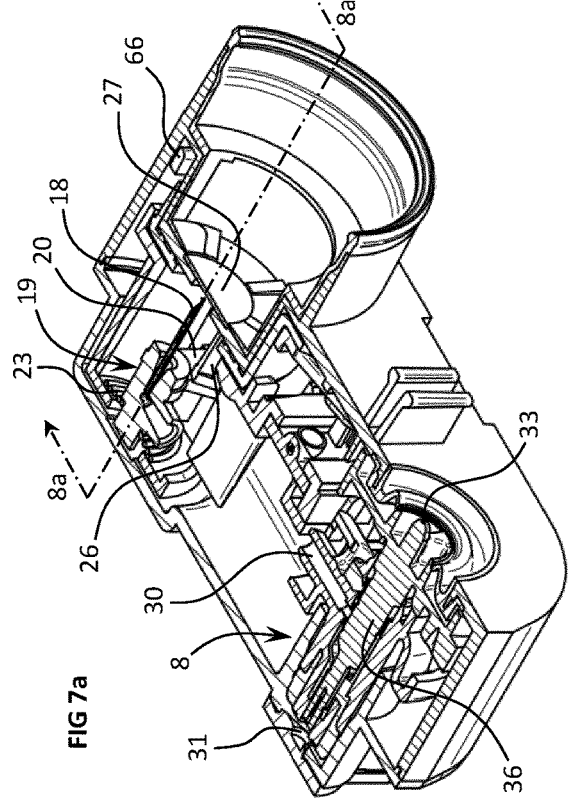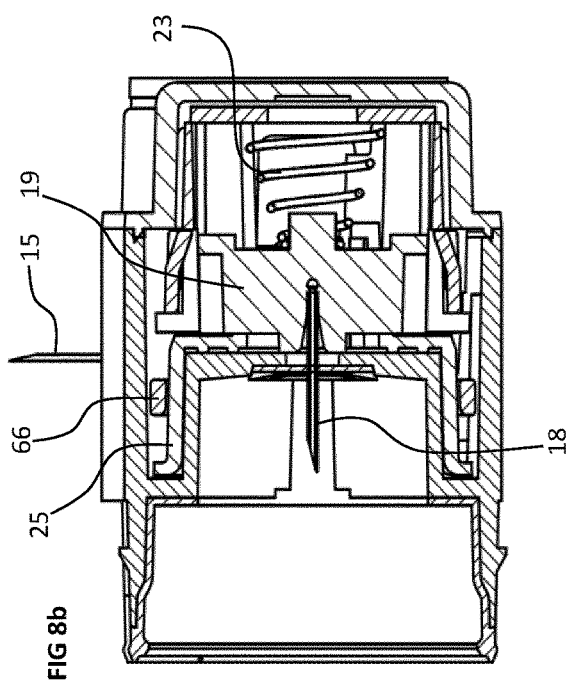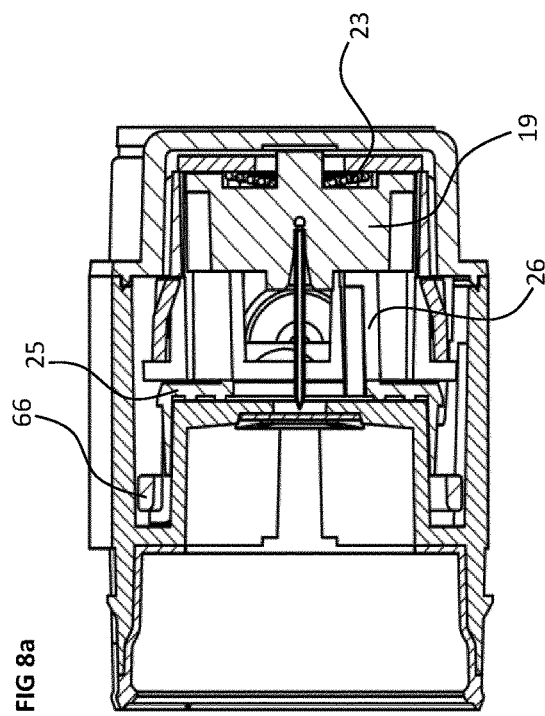

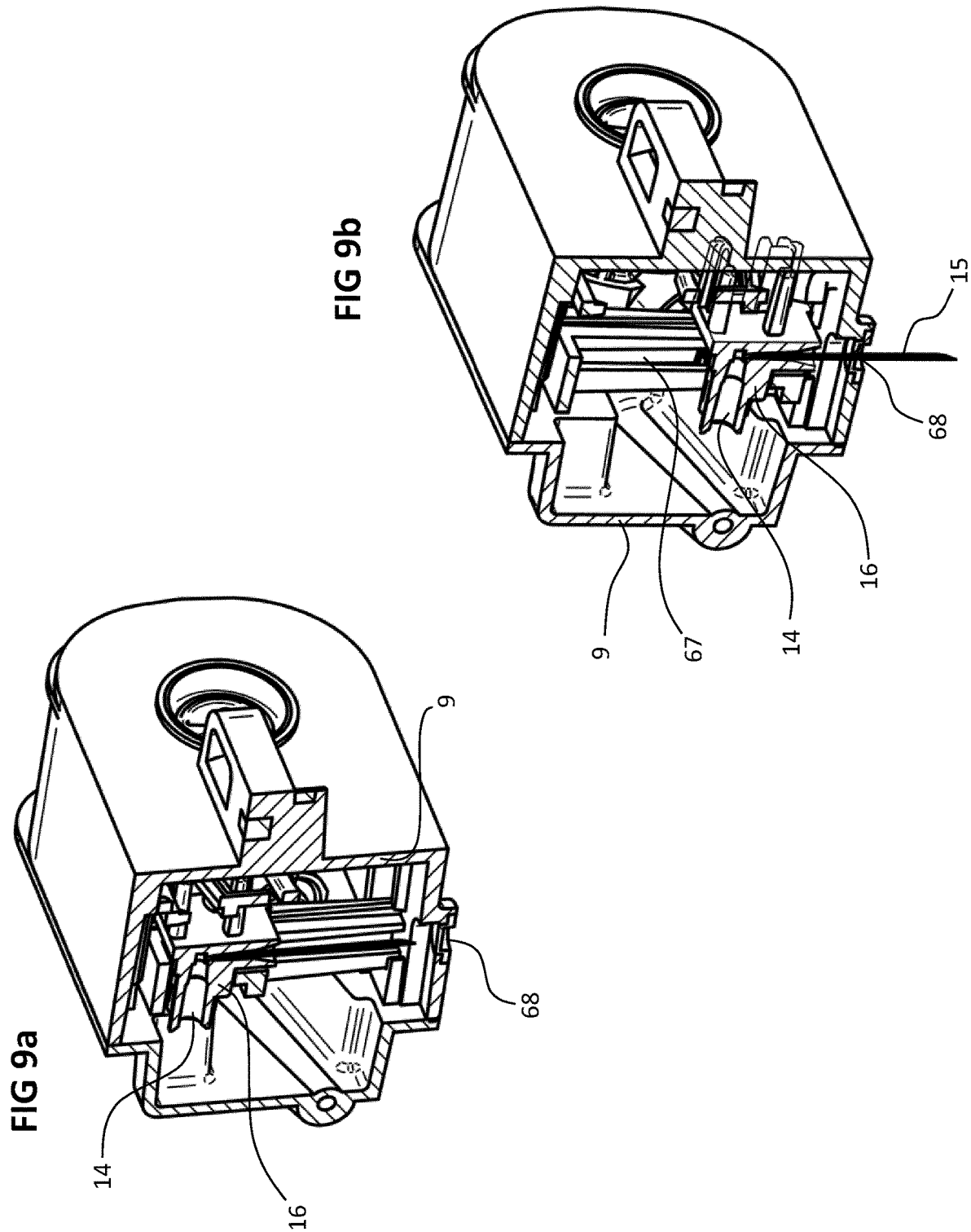

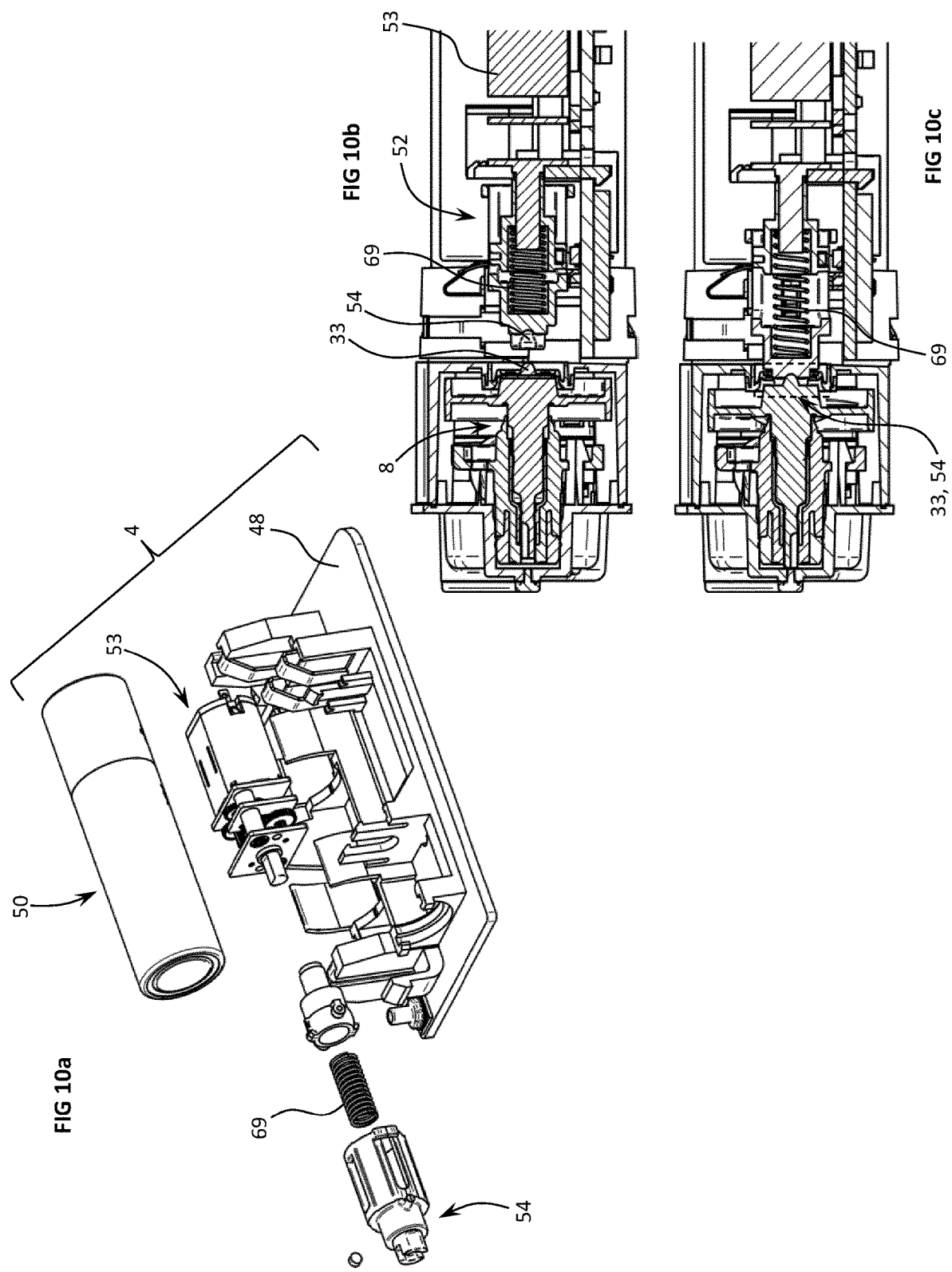

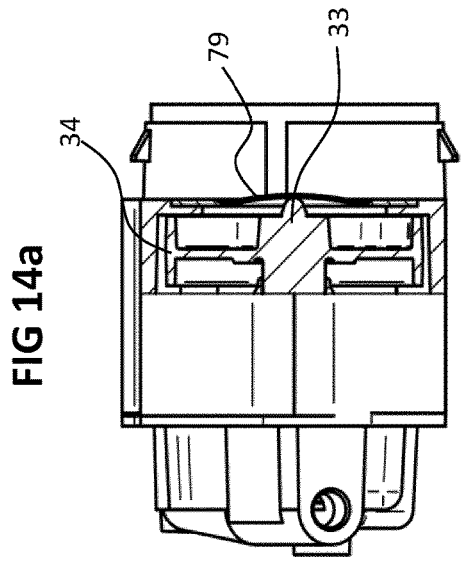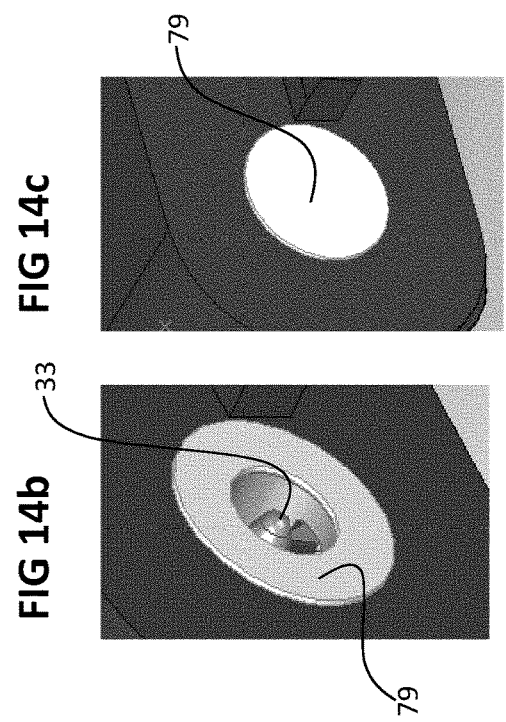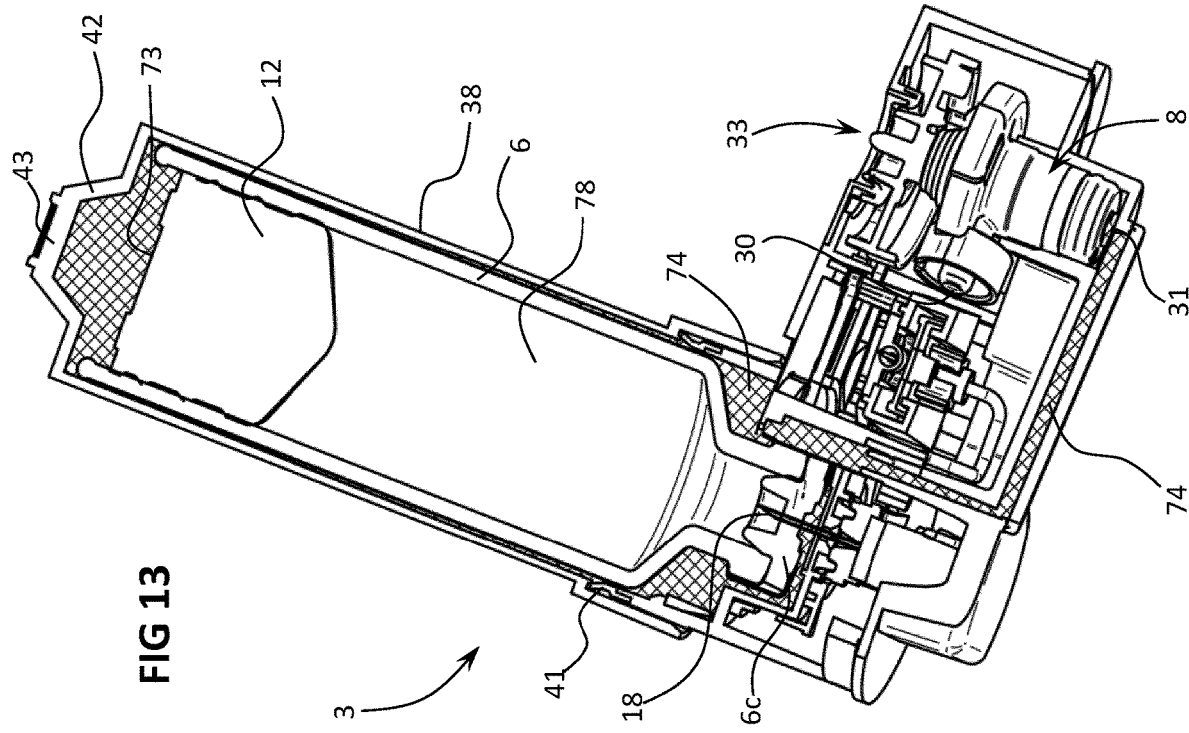

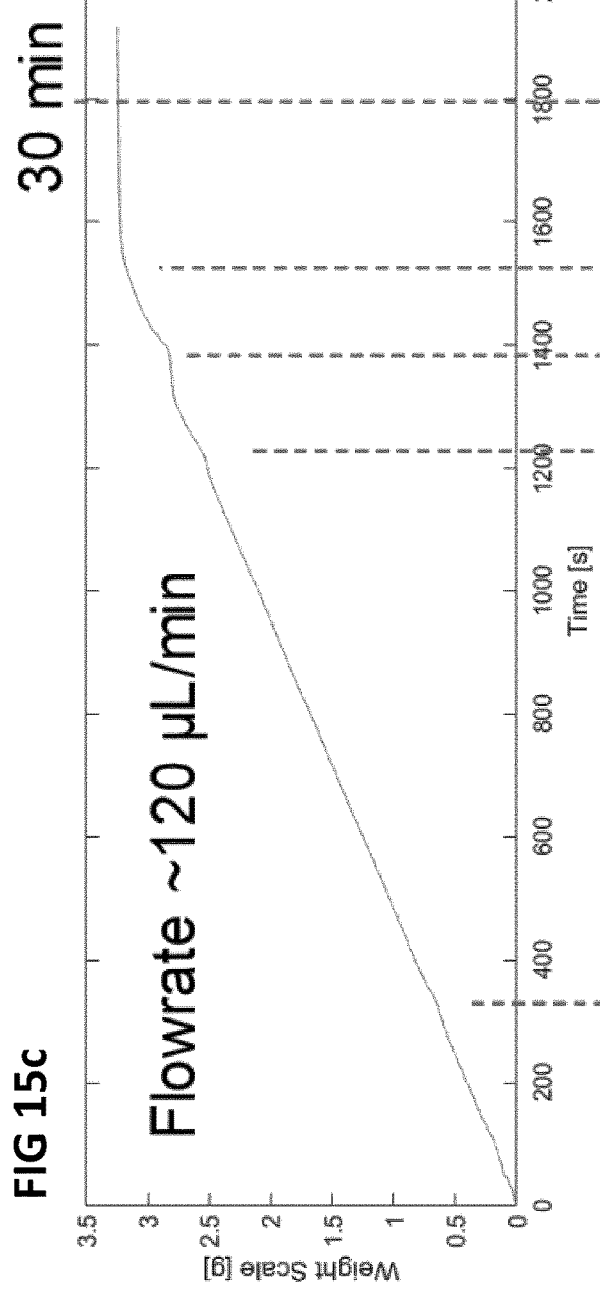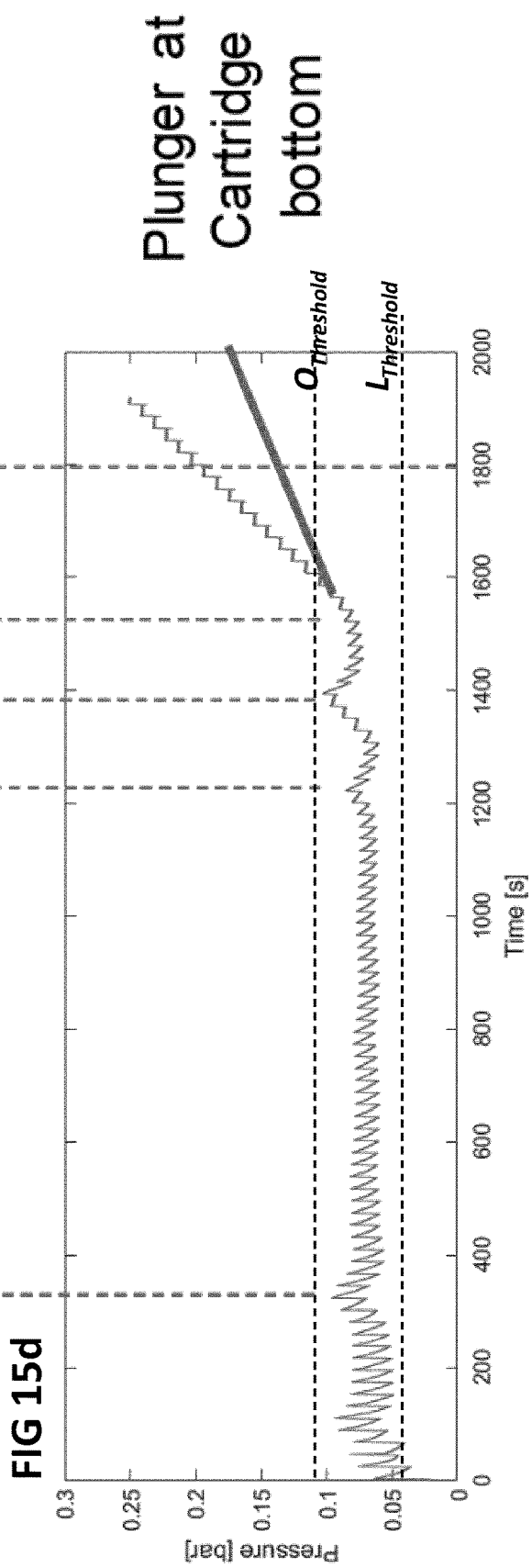

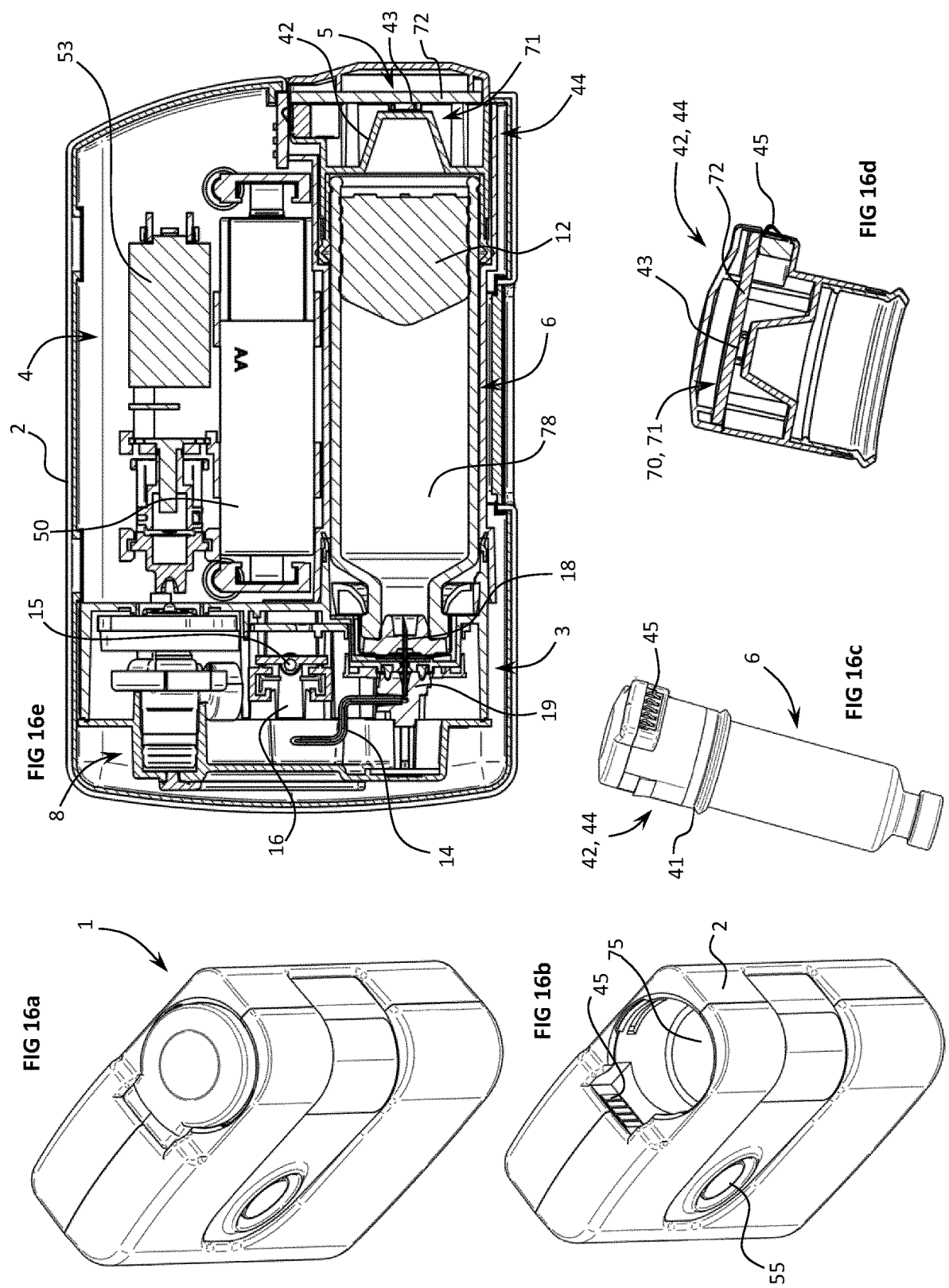

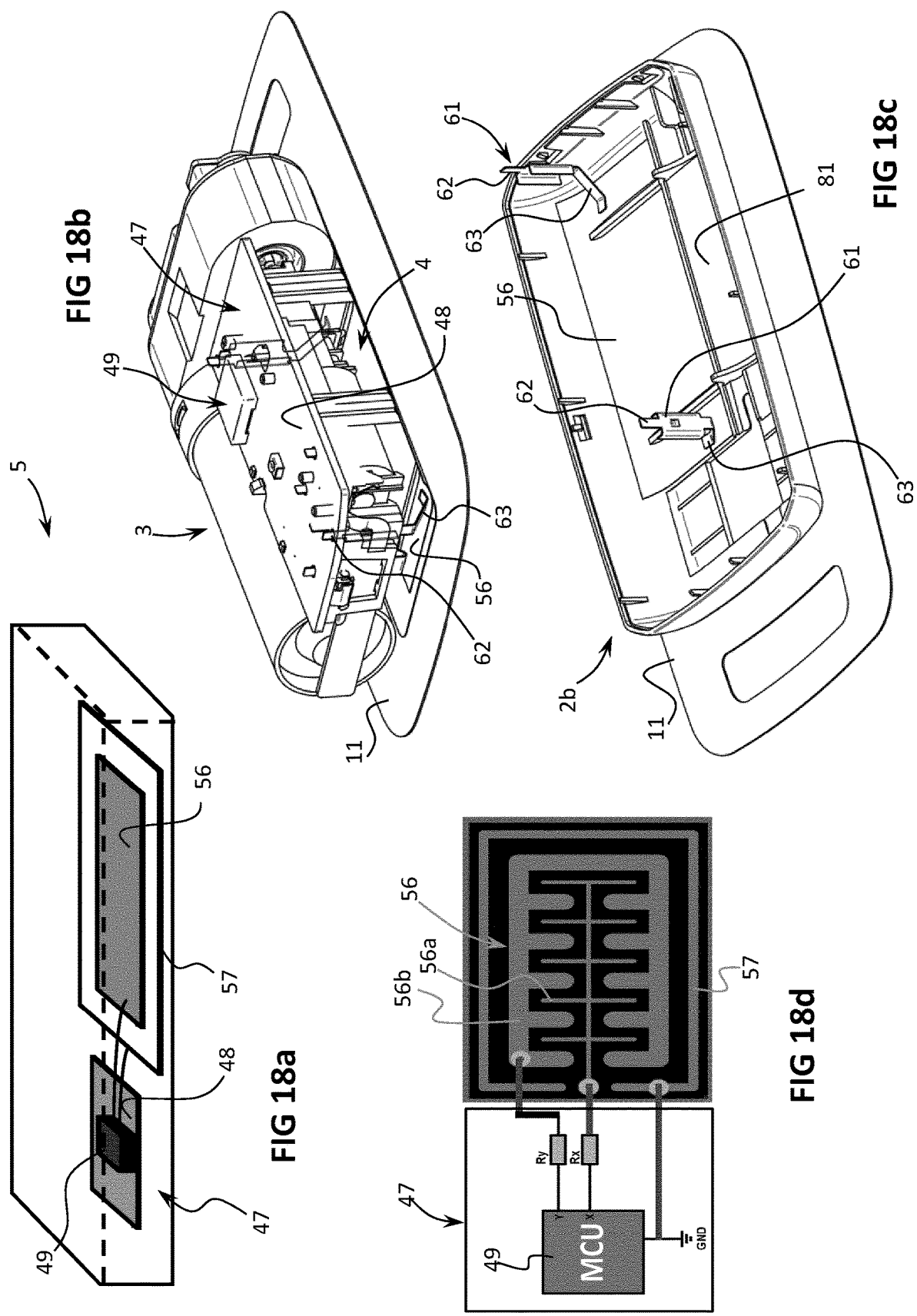

DRUG DELIVERY DEVICE

CROSS-REFERENCE TO RELATED APPLICATION

This application is the U.S. national stage application of International Patent Application No. PCT/EP2022/055835, filed Mar. 8, 2022.

TECHNICAL FIELD

This invention relates to a drug delivery device for subcutaneous administration of a liquid drug. The invention in particular relates to a drug delivery device in the form of a patch device.

DESCRIPTION OF RELATED ART

Drug delivery devices in the form of a patch device for mounting on a patient's skin for subcutaneous delivery of liquid drug are known. Some devices typically receive a cartridge or have an internal reservoir that is filled by the patient/healthcare professional. In this case, the drug is drawn from a vial and transferred into the internal reservoir using a syringe. Since cartridges are widespread and their handling is so much easier, it is advantageous to provide a device that can be employed with standard cartridges. The liquid drug may for instance be a biological medical product or other drugs that are administered merely for single shot administration, within a rather short time depending on the intended use. It is known to provide drug delivery devices in the form of a patch device with a single use disposable component assembled to a reusable component containing drive and control electronics, or as a single disposable component.

The reliability, safety, compactness and ease of use of drug delivery devices worn by a patient is important. For disposable components, the amount of parts and consequently cost of the disposable device is also an important consideration.

In order to satisfy safety and reliability requirements, many conventional patch pump drug delivery devices have complex pump mechanisms and are rather bulky. Also, a long shelf life and adequate sterilization is often difficult to achieve and raises manufacturing costs.

For safety of use of the drug delivery device, it is also important to ensure that it may only be actuated when attached to a patient's skin, and that it remains sterile until administration of the drug.

SUMMARY OF THE INVENTION

In view of the foregoing, it is an object of the invention to provide a drug delivery device, in particular in the form of a patch device, with a disposable unit, or as an entirely disposable device, for administration of a liquid drug that is safe, reliable, and compact.

It is advantageous to provide a drug delivery device that may be used for administration of liquid drugs provided in a drug container with a plunger.

It is advantageous to provide a drug delivery device that is easy to use.

It is advantageous to provide a drug delivery device that is economical to produce.

It is advantageous to provide a drug delivery device that has a long shelf life.

Objects of the invention have been achieved by providing the drug delivery device according to claim 1. Dependent claims set forth various advantageous embodiments of the invention.

Disclosed herein, according to a first aspect of the invention, is a drug delivery device comprising a delivery unit including a drug container, a liquid flow system, a pumping system, and a casing enclosing therein the drug container, the pumping system and at least a part of the liquid flow system. The drug container comprises a barrel portion and a plunger slidably mounted within the barrel portion and sealing the drug within the container at one end of the barrel portion, the liquid flow system connected fluidically to the drug container during delivery of the liquid drug. The drug container is contained in a hermetic manner within a container receiving cavity of a container casing portion of the casing and the container receiving cavity is fluidically interconnected to a fluid outlet of the pumping system in a gas tight manner. The pumping system comprises a fluid inlet connected to environmental air, the pumping system configured to pump environmental air drawn in through the fluid inlet into the container receiving cavity generating a gas pressure within the container casing thus applying pressure on a back end of the plunger for delivery of the liquid drug.

In an advantageous embodiment, the pumping system comprises a pump engine including
  a stator,
  a rotor rotatably and axially slidably mounted at least partially in the stator, the rotor comprising a first axial extension having a first diameter and the second axial extension having a second diameter greater than the first diameter,
  a first valve formed by a first valve seal mounted on the stator around the first axial extension, in conjunction with a first channel in the rotor that is configured to allow fluidic communication across the first valve seal when the first valve is in an open position, and
  a second valve formed by a second valve seal mounted on the stator around the second axial extension, in conjunction with a second channel in a rotor that is configured to allow fluidic communication across the second valve seal when the second valve is an open position.

In an advantageous embodiment, the drug container is a drug cartridge comprising a septum at one end.

Disclosed herein, according to a second aspect, is a drug delivery device comprising:
  a delivery unit including a drug container comprising a barrel portion and a plunger slidably mounted within the barrel portion and hermetically sealing against an inner surface of the barrel portion for containing a liquid drug within the drug container; and
  an electronic control system and a plunger sensing system including an optical sensor comprising a transmitter and a receiver, the transmitter configured for transmitting an optical signal to a back end of the plunger and the receiver configured to receive the optical signal reflected off the plunger back end, the plunger sensing system connected to the electronic control system configured to measure a time of flight of the optical signal from the transmitter to the receiver and to determine therefrom a position of the plunger within the cylinder portion of the drug container.

In an embodiment, the delivery unit comprises a casing including a container casing portion comprising a plunger end portion covering an end of the drug container facing the plunger, the plunger end portion comprising a transparent sensor window allowing an optical signal to pass through the plunger end portion of the container casing, the optical sensor being positioned on or proximate the sensor window, the transmitter configured for transmitting an optical signal through the sensor window to the back end of the plunger and the receiver configured to receive the optical signal reflected off the plunger back end and returning through the sensor window.

In an embodiment, the plunger end portion of the container casing portion comprises a raised portion positioning the sensor window at a certain distance away from the plunger end back end allowing an optical time of flight measurement of the plunger in its initial position.

In an embodiment, said certain distance away from the plunger end back end is in a range of 5 mm to 20 mm.

In an embodiment, the delivery unit comprises a casing including a container casing portion comprising a plunger end portion covering an end of the drug container facing the plunger, the plunger end portion comprising a transparent sensor prism allowing an optical signal to pass through the plunger end portion of the container casing, the optical sensor being positioned on or proximate a face of the sensor prism, the transmitter configured for transmitting an optical signal through the sensor prism to the back end of the plunger and the receiver configured to receive the optical signal reflected off the plunger back end and returning through the sensor prism.

In an embodiment, said face of the sensor prism on which the optical sensor is mounted is substantially orthogonal to the direction of travel of the plunger.

Disclosed herein, according to a third aspect, is a drug delivery device comprising a delivery unit including a drug container, a liquid flow system, a pressurized gas source, and a casing enclosing therein the drug container, the pressurized gas source and at least a part of the liquid flow system. The drug container comprises a barrel portion and a plunger slidably mounted within the barrel portion and sealing the drug within the container at one end of the barrel portion. The drug container is contained within a container receiving cavity of a container casing portion of the casing and the container receiving cavity fluidically interconnected to a fluid outlet of the pressurized gas source in a gas tight manner. The pressurized gas source is configured to supply pressurized gas in the container receiving cavity thus applying pressure on a back end of the plunger for delivery of the liquid drug. The drug delivery device further comprises a pressure sensor fluidically coupled to the container casing for measuring a pressure within the container casing, the pressure sensor connected to an electronic control system configured to measure a pressure detected by the pressure sensor over time and to determine from the pressure measurement over time a position of the plunger over time, including a stop in movement of the plunger either due to occlusion in the drug delivery flow system or an end of travel of the plunger within a container corresponding to a container empty position.

In an advantageous embodiment, the pressurized gas source comprises a pumping system configured to pump a gas into the container receiving cavity thus applying pressure on a back end of the plunger.

In an advantageous embodiment, the pumping system is configured to pump environmental air into the container receiving cavity thus applying pressure on a back end of the plunger.

Disclosed herein, according to a fourth aspect, is a drug delivery device comprising a delivery unit including a drug container in the form of a drug cartridge containing a liquid drug therein, a liquid flow system, a pumping system and a casing within which the drug container, the pumping system and at least a part of the liquid flow system are mounted. The drug container comprises a septum sealing an end of the drug container. The liquid flow system comprises an injection delivery system including an injection needle configured for injection of the drug in an actuated state of the drug delivery device, the liquid flow system further comprising a container fluidic connection system including a septum needle mounted on a movable septum needle support, a spring pressing the septum needle support towards the septum of the drug container, and a blocking organ movable from a blocking position in which the septum needle support is held in a retracted position where the septum needle is not in contact with the septum, to an actuated position in which the septum needle support is released and allowed to travel towards the drug container septum such that the septum needle pierces through the septum under the force of the spring.

In an advantageous embodiment, the blocking organ comprises a rotatable support ring and a blocking finger extending from the support ring and rotatably movable with the support ring from a position in which the blocking finger engages the septum needle support and maintains it in the retracted position, to an actuated position in which the blocking finger disengages the septum needle support to allow it to travel to an actuator position where the septum needle pierces through the septum.

In an advantageous embodiment, the septum needle support comprises flange sections and a gap between the flange sections, the blocking finger engaging the flange section during the blocked position in which the septum needle support is retracted.

In an advantageous embodiment, the septum needle support comprises guides on opposite sites engaging complementary guide portions in the casing for slidably guiding the septum needle support from the retracted position to the septum piercing position.

In an advantageous embodiment, the injection delivery system comprises an needle actuation mechanism configured to move the injection needle from a retracted position within a housing of the drug delivery device to an extended delivery position where the injection needle projects through a base wall of the housing, the needle actuation mechanism comprising a rotary actuation disc configured to engage an actuation lever coupled to the slidable septum needle support for transfer between retracted and extended delivery positions.

In an advantageous embodiment, the actuation disc is directly coupled or integrally formed with a rotor of a pump engine of the pumping system.

In an advantageous embodiment, the actuation lever is coupled to the blocking organ to move it from the locked position to the unlocked position.

In an advantageous embodiment, the actuation lever comprises a support ring mounted around a shroud portion of the casing surrounding a cavity receiving the septum end of the drug container therein.

In an advantageous embodiment, the actuation lever comprises a lever arm extending from the rotatably support ring configured to engage an indent in the actuation disc upon initial actuation of the drug delivery device.

Disclosed herein, according to a fifth aspect, is a drug delivery device comprising a housing, a delivery unit including a drug container, and a control unit mounted within the housing, the control unit comprising an on-body sensing system including an electrode connected to an electronic control system of the control unit for measuring a capacitance value configured to detect whether the drug delivery device is positioned against a patient's skin. A skin contact wall of the housing has an inner side facing an inside of the housing in which the delivery unit and control unit are mounted, and an outer mounting side facing the outside of the housing and intended to be placed against the skin of a patient. The electrode comprises a layer of metal mounted directly against the inner side of the skin contact wall.

In an advantageous embodiment, the metal layer of the electrode consists of a metal layer directly deposited on said inner surface of the skin contact wall.

In an advantageous embodiment, the direct deposit metal layer is a galvanic plating layer.

In an advantageous embodiment, the on-body sensing system further comprises a shield in the form of a conductor surrounding the electrode.

In an advantageous embodiment, the on-body sensing system is configured to measure a capacitance value between said electrode and a ground value.

In an advantageous embodiment, the on-body sensing system comprises a second electrode insulatingly separated from said electrode which constitutes a first electrode, a potential between the first electrode and second electrode being measured to determine a capacitance value.

In an advantageous embodiment, the second electrode is formed as a metal layer directly on the inner side of the mounting wall.

In an advantageous embodiment, the second electrode is formed as a metal layer in the same manner as the first electrode.

In an advantageous embodiment, the second electrode and first electrode have interleaving portions.

Disclosed herein, according to a sixth aspect, is a method of producing a drug delivery device comprising
- a prefilled drug container, wherein the drug container comprises a barrel portion and a plunger slidably mounted within the barrel portion and sealing the drug within the container,
- a fluidic pack including a liquid flow system providing a fluidic connection from the drug container to a patient during a drug delivery action of the drug delivery device,
- a control unit comprising electronic parts, and
- a housing,
the method comprising the following steps
- a) assembling components of the fluidic pack to form said fluidic pack,
- b) sterilizing the fluidic pack,
- c) providing said prefilled drug container,
- e) assembling the fluidic pack to the prefilled drug container to form a container pack system,
- f) assembling the container pack system to the control unit and the housing (2) to form the drug delivery device, characterized in that steps c) and e) are performed in aseptic conditions.

In an advantageous embodiment, step f) is not performed in aseptic conditions.

In an advantageous embodiment, the cartridge pack system comprises a container casing which encompasses the prefilled drug container.

In an advantageous embodiment, the container pack system comprises a pump system.

In an advantageous embodiment, the pump system comprises a coupling interface of the pump system of the delivery unit, the pump drive providing torque to the rotor of the pumping system wherein the coupling interface is sealed by a sealing membrane to maintain sterility after step b).

In an advantageous embodiment, the housing comprises a user interface.

In an advantageous embodiment, the sterilization method of the b) is any of gamma radiation, ETO sterilization, NO2 sterilization, steam sterilization, VHP sterilization, X-ray sterilization or e-beam sterilization.

In an advantageous embodiment, the assembly steps of step e) comprise a form-fit connection.

In an advantageous embodiment, the form-fit connection provides a hermetical sealing of the prefilled drug container within the container pack system.

In embodiments of the method, the delivery unit described herein without the drug container assembled therein forms said fluidic pack, the delivery unit with the drug container assembled therein forms said container pack, and the drive unit described herein forms said control unit comprising electronic parts.

In embodiments of the method, the drug delivery device may have any one or more additional features of any of the embodiments of the device described herein.

In various embodiments, the drug container may comprise a septum at one end of the drug container, the septum being perforated by a septum needle fluidically connected to the injection needle during actuation of the drug delivery device.

In various embodiments, the drug delivery device may comprise an injection needle mounted on a movable needle support configured to move the needle from a retracted position where it is fully within the housing, to an actuated position where the needle tip projects out of a skin contact wall of the housing for injection delivery of the liquid drug.

In various embodiments, the liquid flow system may comprise an injection delivery system including the injection needle mounted on a movable needle support, connected via a conduit to a container fluidic connection system including the septum needle.

In various embodiments, the drug delivery device may further comprise a drive unit comprising a pump drive having a coupling interface coupling to a drive coupling interface of the pumping system of the delivery unit, the pump drive providing torque to the rotor of the pumping system.

In various embodiments, the drug delivery device may comprise a housing within which the delivery unit and the drive unit is assembled, the housing comprising a skin contact wall for mounting against a patient's skin, the skin contact wall comprising an adhesive patch with a protective film.

In various embodiments, for certain medical applications, the drug delivery device may be configured as a single use disposable device, and may in particular be configured for a single dose administration of the liquid drug contained in the container.

Further objects and advantageous features of the invention will be apparent from the claims, from the detailed description, and annexed drawings, in which:

BRIEF DESCRIPTION OF THE DRAWINGS

FIG. 1a is a perspective view of a drug delivery device according to an embodiment of the invention;

FIG. 1b is a perspective view of the device of FIG. 1a with the cover and adhesive with protective film exploded away;

FIG. 2 is an exploded view of the embodiment of FIG. 1b with the cover and adhesive with protective film removed, showing a housing base, delivery unit, and drive unit;

FIG. 3a is an exploded view of the drive unit of FIG. 2 according to an embodiment of the invention showing a drug container within the drive delivery unit;

FIGS. 3b and 3c are perspective cross-sectional views of the delivery unit according to an embodiment of the invention;

FIG. 4a is a perspective view of a pump and liquid flow system of a delivery unit of a drug delivery device according to an embodiment of this invention;

FIGS. 4b and 4c are perspective exploded views of the liquid flowing pumping system of FIG. 4a;

FIGS. 5a to 5e are cross-sectional views of a liquid flow and pumping system of a drug delivery device according to an embodiment of the invention, showing different steps in the actuation of a needle of a transcutaneous delivery system and a needle of a container fluidic connection system upon actuation of the drug delivery device;

FIG. 6a is a perspective view of the device of FIG. 5a (with an outer housing part removed to better see inside) in an initial position corresponding to FIG. 5a;

FIG. 6b is a view similar to FIG. 6a showing an intermediate actuated position corresponding to FIG. 5c;

FIG. 6c is a view similar to FIG. 6b, with a portion of housing added in cross section, showing the position corresponding to FIG. 5e which is an end position where both needles are fully inserted;

FIG. 6d is a perspective view of the device of FIG. 6a from an opposite side;

FIG. 6e is a view similar to FIG. 6d showing an intermediate actuated position just as the septum needle is about to be released;

FIG. 6e is a view similar to FIGS. 6d and 6f, 6f showing an end position where both needles are fully inserted;

FIG. 7a is a perspective cross-sectional view through lines 7a-7a of FIG. 5a;

FIG. 7b is a cross-sectional I view through line 7b-7b of FIG. 5e;

FIG. 8a is a cross-sectional view through line 8a-8a of FIG. 7a;

FIG. 8b is a cross-sectional I view through line 8b-8b of FIG. 7a;

FIG. 9a is a cross-sectional view through line 9a-9a of FIG. 5a;

FIG. 9b is a cross-sectional view through line 9b-9b of FIG. 5e;

FIG. 10a is a perspective exploded view of a drive unit of a drug delivery device according to an embodiment of the invention;

FIG. 10b is a cross-sectional view of a portion of a drug delivery device according to an embodiment of the invention showing a drive unit in an uncoupled state with a delivery unit of a drug delivery device according to an embodiment of the invention;

FIG. 10c is a view similar to FIG. 10b showing a coupled state;

FIG. 11b is a c cross-sectional I view through lines 11b-11b of FIG. 11a;

FIG. 12a is a perspective view of a variant of the device of FIG. 11a;

FIG. 12b is a cross-sectional view through lines 12b-12b of FIG. 12a;

FIG. 13 is a cross-sectional view of a liquid flow and pumping system of a drug delivery device according to an embodiment of the invention, showing an air flow system of a pneumatic drive;

FIG. 14a is a partial cross-sectional view illustrating a sealing membrane covering a pump engine coupling interface of the device of FIG. 13;

FIG. 14b is a perspective view of a first embodiment of the sealing interface;

FIG. 14c is a perspective view of the second embodiment of the sealing interface;

FIG. 15c is a schematic illustration of a plot of a flow rates of a drug overtime measured by a pneumatic plunger sensing system according to an embodiment of the invention;

FIG. 15d is a corresponding plot of an air pressure overtime within a container holder of the drug delivery device;

FIG. 16a is a perspective view of the drug delivery device according to an embodiment of the invention;

FIG. 16b is a perspective view of the drug delivery device of FIG. 16a with a drug container removed or prior to insertion in the drug delivery device;

FIG. 16c is a perspective view of the drug container and a closing cap mounted on a plunger of the drug container for insertion in the drug delivery device of FIG. 16b;

FIG. 16d is a cross-sectional view of the drug container cap of FIG. 16c;

FIG. 16e is a cross-sectional view of the embodiment of FIG. 16a;

FIG. 18a is a schematic illustration of an on-body sensing system of a drug delivery device according to an embodiment of the invention;

FIG. 18b is a perspective illustration of a delivery unit coupled to a drive unit of a drug delivery device according to an embodiment of the invention illustrating components of the on-body sensing system;

FIG. 18c is a perspective view of a housing cover of a drug delivery device illustrating components of on-body sensing system according to embodiments of this invention;

FIG. 18d is a schematic illustration of an on-body sensing system of a drug delivery device according to an embodiment of the invention with two electrodes;

DETAILED DESCRIPTION OF EXEMPLARY EMBODIMENTS

Figure 4C:
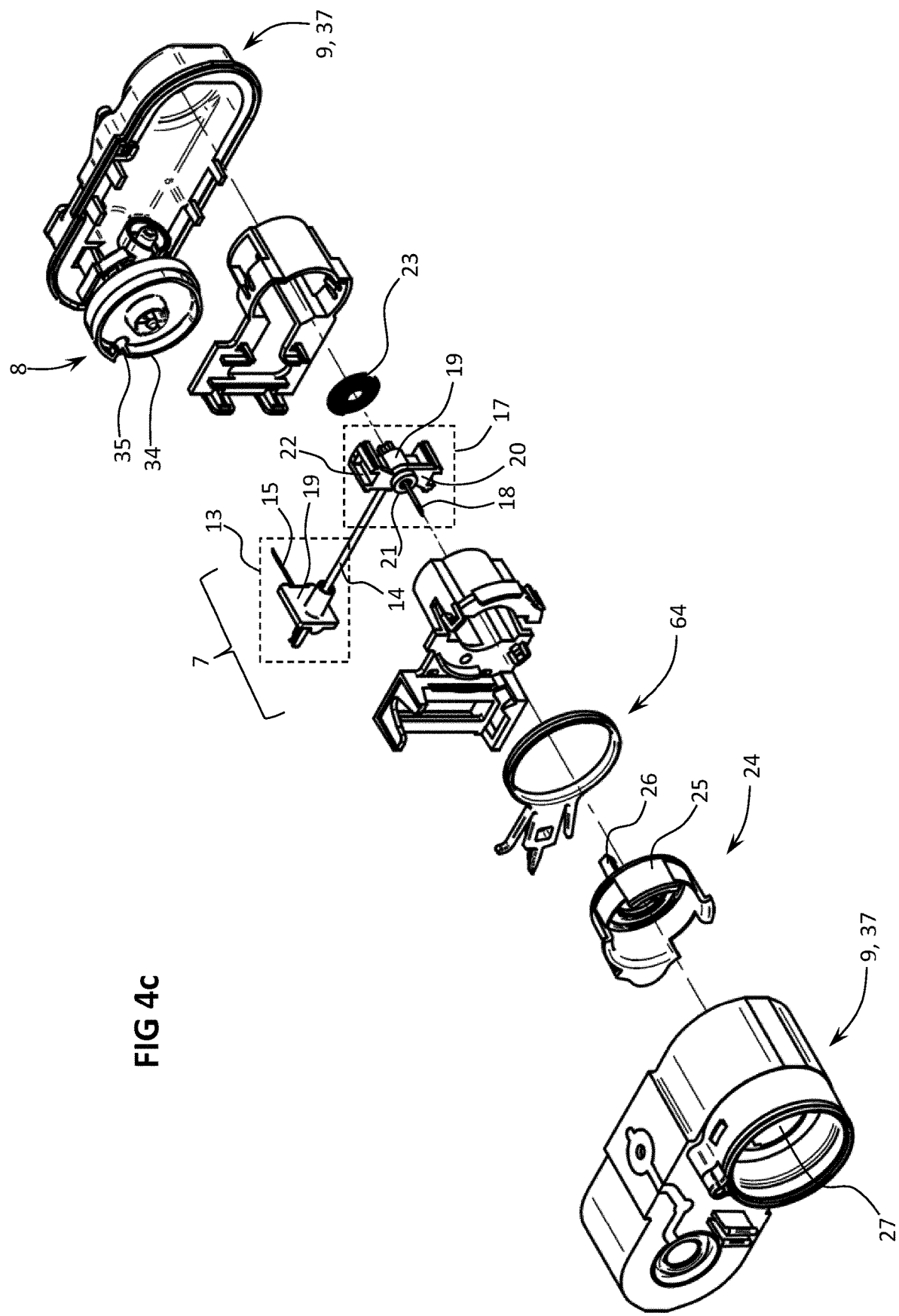
Figure 11A:
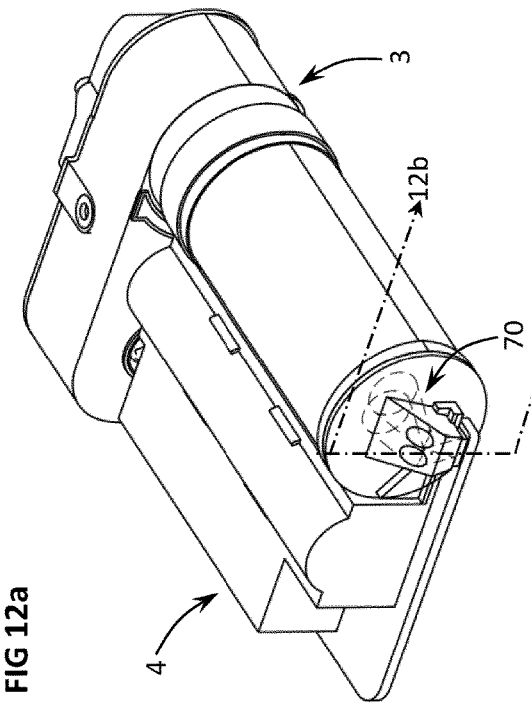
FIG. 11a is a perspective view of a drug delivery device according to an embodiment of the invention with the housing removed, showing a delivery unit and drive unit assembled, together illustrating schematically a plunger sensing system according to first variant.
Figure 12A:
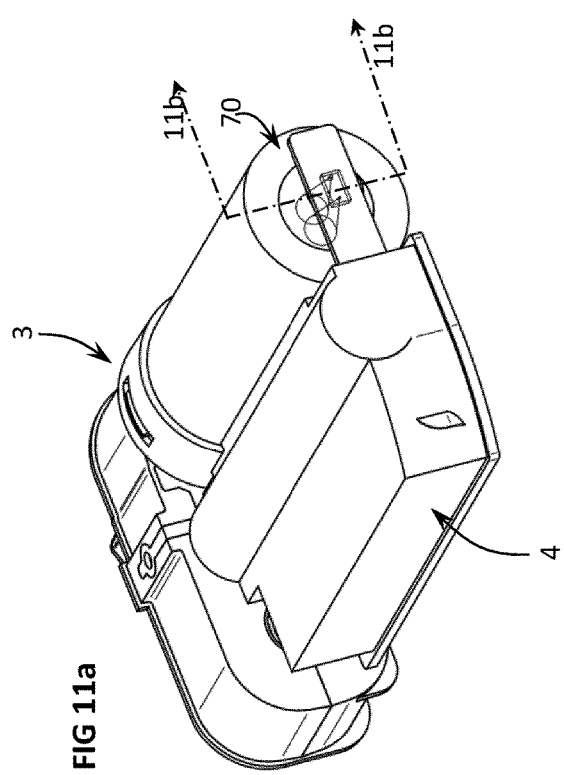
Figure 11B:
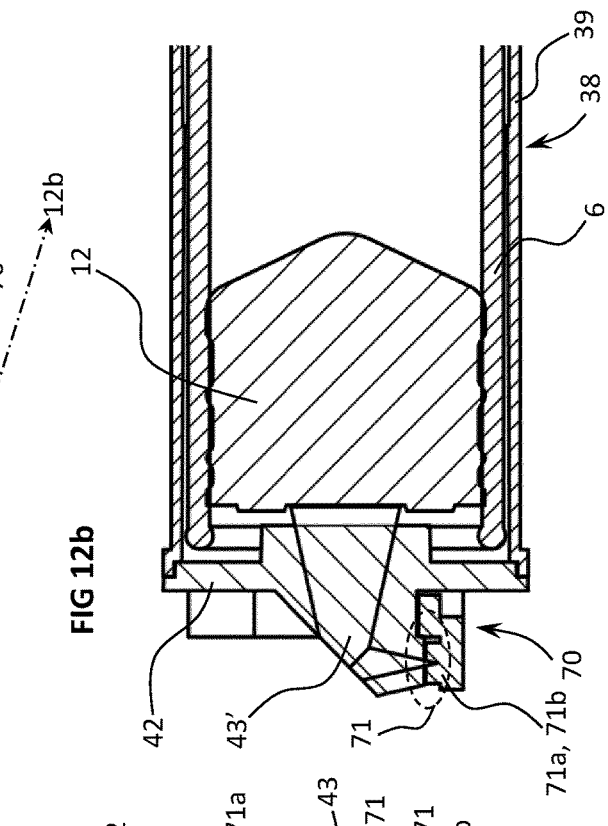
Figure 12B:
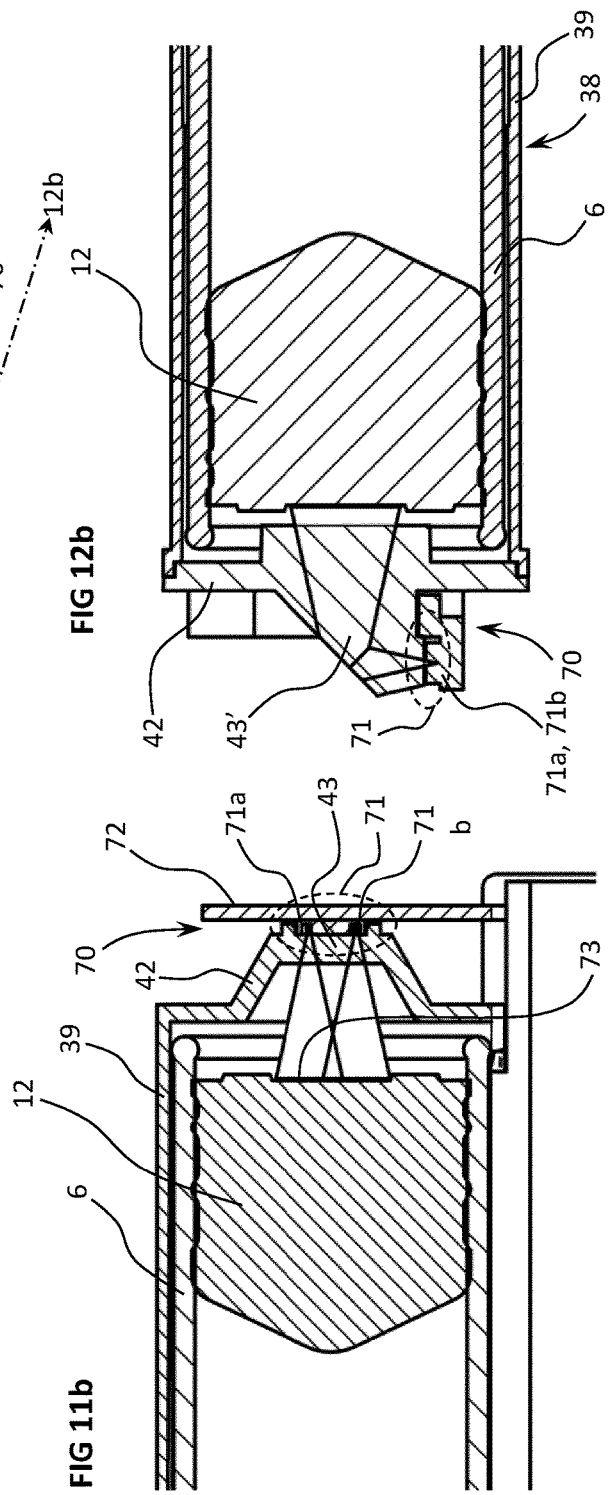

Referring to the figures, a drug delivery device 1 according to embodiments of the invention comprise a housing 2, a delivery unit 3, and a control or drive unit 4, the delivery unit 3 and the control or drive unit 4 being assembled within the housing 2. The housing 2 may be made of two or more parts allowing assembly of the delivery unit, drive unit and any other components within the housing.

In the illustrated embodiments, the drug delivery device 1 is a single use disposable unit for subcutaneous administration of a liquid drug (medicament). The administration may occur in a single dose over a short period of time, typically less than 1 hour, for instance around 30 minutes or less. A single use disposable drug delivery device may also be used for subcutaneous injection of a liquid drug over an extended period of time from a few hours to a few days or even up to 1 to 3 weeks. Depending on the volume of the drug to be injected, the drug delivery device may also be configured to inject the liquid drug within a few minutes.

There are various applications in which it is advantageous to provide a patient in need of a drug with a drug delivery device that the patient may wear on the patient's body, or that allows a patient to apply the device directly on his/her skin prior to use, for injection of a drug outside of a hospital or medical institution, for instance at home. For certain medical applications, there may also be the need to deliver a liquid drug within a range of time subsequent to an occurrence such as a surgical intervention, or other form of treatment in a hospital or clinic, for instance once the patient is back at home. There may also be applications in which it would be advantageous to supply the patient with a drug delivery device for injection of a medicament at certain times, for instance once a week or once a month or various other intervals depending on the drug and the treatment, without requiring the patient to have the drug administered by a healthcare professional in a clinical environment, for instance to allow the patient to perform treatment at domicile.

Although the embodiments shown in the figures concern a single use disposable drug delivery device, within the scope of the invention for various aspects described herein, a drug delivery device with a disposable portion that may be assembled to a reusable portion comprising a drive unit, electronics and power supply may also be used. The delivery unit 3 may be mounted in a housing of the drug delivery device and the drive unit 4 in a separable housing portion such that the drive unit 4 can be reused with subsequent delivery units. An example of a drug delivery device with single use disposable and reusable parts is described for instance in WO 2020109409.

The drug delivery device includes a user interface 55 that may include one or more buttons for actuating the drug delivery device, light and/or sound status indicators, and optionally a screen or other display for presenting information to an operator of the device.

Drug delivery devices according to embodiments of the invention may advantageously be configured as a patch device for mounting on a patient's skin. An adhesive layer (not shown) may be provided on an outer surface of a skin contact wall 81 of the housing 2, for instance on a surface of the cover 2b, covered by a protective film that may be peeled off the adhesive layer prior to placing the adhesive layer on the patient's skin at the site of injection. A needle orifice 10 through the skin contact wall 81 is covered by the protective film 11 prior to use, and allows a transcutaneous injection needle 15 to extend therethrough and pierce the patent's skin upon activation of the drug delivery device 1.

The delivery unit 3 comprises a drug container 6, for instance a drug cartridge, containing a liquid drug 78, a liquid flow system 7 for channeling the liquid drug to a patient subcutaneously, a pumping system 8, and a casing 9 for housing the drug container, the liquid flow system 7 and pumping system 8.

In embodiments, the casing 9 may be configured to enclose the drug container in a hermetic manner such that a gas pressure within the casing portion around the drug container may be generated for effecting the pumping action of the drug as will be described in more detail herein.

The drug container 6 may be of a conventional type of drug cartridge comprising a container having a barrel portion 6a, a neck portion 6b having an open end closed by a septum 6c, and a plunger 12 closing an open end of the barrel portion 6a, the liquid drug 78 to be administered to the patient being contained hermetically within the barrel portion 6a between the plunger and the septum. Such drug containers 6 are well-known in the pharmaceutical industry and may be used for containing in a sterile manner many different types of liquid drugs. Such drugs may also be provided in different sizes (volumes), it being understood that a drug delivery device according to embodiments of the present invention may be adjusted in dimensions to cater for different types of drug containers depending on the medical application. Embodiments of the invention may also be used with non-standard drug containers.

Although certain aspects of the invention disclosed herein require drug containers comprising a sliding plunger, it may be noted that certain other aspects of the invention disclosed herein are not limited for use to drug containers with plungers and may be used with other forms of drug containers without plungers. For instance an on-body sensing system, as will be described further on, is independent of the type of drug container that is used in the drug delivery device. Also, for instance, the container fluidic connection system 17, as will be described further on, requires a drug container with a pierceable sterile barrier, but does not necessarily require a drug container with a plunger. In addition, a method of producing a drug delivery device, as will be described further on, is independent of the type of drug container that is used in the drug delivery device.

The delivery unit 3 incorporates the pumping system 8 that causes liquid from the container to be pumped to the injection needle 15 once the drug delivery device has been activated. The pumping system comprises a drive coupling interface 33 that couples to a coupling interface 54 of a pump drive 52 of the drive unit 4. The drive unit thus provides the mechanical power via the coupling 54, 33 to drive the pumping system 8.

The pump engine 28 may advantageously comprise a design and configuration similar to the pump engine described in WO 2007074363 or WO 2015015379 in which a rotor 32 is mounted within a stator 29 and is rotatably and axially removable within the stator in order to pump a fluid from a fluid inlet 30 to a fluid outlet 31. As known from the above-mentioned publications, the rotor 32 has a pump shaft 36 with first and second diameters surrounded by seals that open and close a fluid channel between the inlet and outlet as the rotor rotates and axially displaces due to a cam mechanism between the stator and rotor, whereby during the opening and closing of the valves between the fluid inlet and pumping chamber, respectively between the pumping chamber and outlet, a pumping action is performed.

In summary, the pump engine 28 according to a preferred embodiment includes:
  the stator 29,
  a rotor 32 slidably and rotatably mounted at least partially in the stator, the rotor comprising a first axial extension having a first diameter and a second axial extension having a second diameter greater than the first diameter, a first valve formed by a first valve seal mounted on the stator around the first axial extension, in conjunction with a first channel in the rotor that is configured to allow liquid communication across the first valve seal when the first valve is in an open position, a second valve formed by a second valve seal mounted on the stator around the second axial extension, in conjunction with a second channel in the rotor that is configured to allow liquid communication across the second valve seal when the second valve is an open position.

Although the pump engine design in general and the pumping action principle may be understood by referring to the above-mentioned publications, in embodiments of the present invention, the pumping system is not fluidically connected to the liquid to be administered. Rather, in embodiments of the present invention the pump engine may advantageously be used to pump air that creates a pressure on the container plunger to displace the plunger and press liquid out of the container once the septum is pierced.

In advantageous embodiments of the invention, in particular for single use and single injection of the contents of the drug container, for instance over time spanning a few minutes to 60 minutes, the pump engine may be used to pump air that generates a pressure on the plunger 12 in order to advance the plunger towards the septum and push the liquid 78 within the container via the liquid flow system 7 through the injection needle 15 of a subcutaneous delivery system 13. In these embodiments, the pumping system 8 thus acts as a pneumatic drive generating air pressure within at least a portion of the casing 9 behind the plunger 12 as best illustrated in FIG. 13.

An important advantage of using such pump engine in embodiments of the present drug delivery device is that there is no direct connection of fluid between the inlet and outlet at any position of the rotor and no actuation of any valves are required, such that a particularly reliable pumping of gas without leakage is ensured in an easy to operate arrangement. The pump engine 28 is very compact and can be driven directly by a rotary electrical motor 53 of a pump drive 52 in the drive unit 4 without gearing. In effect, because of the differential pumping volume displacement that is defined by the axial displacement of the rotor and the difference between the first and second diameters of the pump shaft, the pumping volume displacement rotation can be easily configured for optimal operation with an electrical motor of a given type rotating with a constant speed. Moreover, the pump engine parts can be made entirely of polymer materials and the rotor may be easily coupled to the pump drive ensuring a sterile barrier between the fluidic portion of the pump engine and the coupling interface.

It may be noted that certain aspects of embodiments of the invention described herein do not necessarily rely on a pneumatic drive for their functioning. For instance the on-body sensing system 5 and the plunger sensing system 70 using optical sensors 71 do not necessarily need a pneumatic drive and can also be implemented in drug delivery devices in which the pump engine acts directly on the liquid drug as described for instance in WO 2015015379 in a conventional manner, or using other pump systems per se known in the art that act directly to draw the liquid from the container. Also, the container fluidic connection system 17, that will be described in more detail hereinafter, may also be implemented with different pumping systems, for instance a pneumatic drive, or a drive that presses on the plunger mechanically as per se known, or by drawing the liquid using the engine described in WO 2015015379.

The drive unit 4 is configured to drive principally the pumping system 8 of the delivery unit 3, but may also have additional functions such as processing sensing signals, and transmitting and receiving data from an external device via a wireless communication link, for instance using Bluetooth.

The drive unit 4 comprises an electronic control system 47 that may include a circuit board 48 on which is mounted electronic components including at least one microprocessor 49 and optionally a wireless connection module. The electronic control system further comprises a power source 50 for instance in the form of a battery, and a pump drive 52 including an electrical motor 53.

An axis of the motor 53 may be coupled to a coupling interface 54 configured to engage a complementary coupling interface 33 of the pump engine rotor 32 on the delivery unit 3. If the pump engine 28 is configured with a rotatably and axially movable rotor as discussed above, in a preferred embodiment, the drive coupling interface 54 may be axially slidable with respect to the motor output shaft and biased by means of a spring 69 that presses the motor drive coupling interface 54 against the coupling interface 33 of the pump engine rotor 32 as best illustrated in FIGS. 10a to 10c.

The drive unit may further comprise a plunger sensing system 70 for sensing the position of the container plunger. The plunger sensing system is for determining correct operation of the drug delivery device and identifying for instance occlusion in the liquid flow system, or an end of travel of the plunger when the drug container is empty at the end of the drug administration process. Embodiments of the plunger sensing system 70 will be described in more detail further on.

It may be noted that the plunger sensing system 70 for sensing the position of a plunger according to embodiments of the invention may be implemented on various drug delivery systems having drug containers comprising a plunger, for instance on syringe devices, autoinjectors, pen injection systems (like insulin pens) or any other plunger movement of a primary packaging of fluid medicaments.

The drive unit may further comprise an on-body sensing system 5 for detecting whether the drug delivery device is positioned against the skin of a patient. The on-body sensing system prevents operation of the drug delivery device if it is not positioned against a patient's skin, and may also detect if the drug delivery device is removed before complete delivery of the drug. Embodiments of the on-body sensing system 5 will be described in more detail further on.

The liquid flow system 7 comprises a subcutaneous delivery system 13 including an injection needle 15 for piercing through the skin of a patient and a container fluidic connection system 17 including a septum needle 18 for piercing through the septum 6c of the container 6 upon actuation of the drug delivery device. The subcutaneous delivery system comprises a needle support 16 which is slidably mounted within the housing 2 along a housing slide 67, the needle being mounted on the needle support and movable with the needle support 16 from a fully retracted position within the casing 9 of the delivery unit 3 as illustrated in FIGS. 6a, 6d and 9a to a fully extended position during drug administration as illustrated in FIGS. 6c, 6f and 9b.

The fluidic channel within the needle and needle support is connected to a conduit 14 that may advantageously be in the form of a supple tube allowing the sliding movement of the needle support from the retracted to the extended positions, the tube being connected at its other end to the container fluidic connection system 17.

The container fluidic connection system 17 comprises a septum needle support 19 on which the septum needle 18 is mounted, the septum needle support 19 being slidably mounted within the housing, configured from moving from a retracted position as illustrated in FIGS. 6a, 6d, 7a, and 8a, to an extended position, as illustrated in FIGS. 6c, 6f, 7b, and 8b. In the retracted position, the septum needle 18 is not in contact with the drug 78 within the drug container, and in the extended position the septum needle has pierced through the sealing member 27 (sterile barrier) and septum 6c of the drug container and is in contact with the liquid 78 within the container.

In an advantageous embodiment, the container fluidic connection system 17 may be actuated at the same time as the subcutaneous delivery system 13. It may however be noted that within the scope of the invention, it would be possible to actuate the container fluidic connection system 17 prior to actuation of the subcutaneous delivery system 13, for instance in a sequential manner. The step of first connecting the septum needle 18 with the liquid of the drug, prior to piercing of the patient's skin with the injection needle 15, could allow the fluidic connection comprising the conduit 14 to be filled with drug prior to injection, in order to remove air from the fluidic channels prior to injection.

The container fluidic system 17 in an advantageous embodiment comprises a slidable needle support 19 having flange sections 20 with guides 22 at outer extremities that engage slidably in complementary guides in a housing portion of the casing 9. The container fluidic connection system 17 further comprises a blocking organ 24 with a blocking finger 26. In a locked position in which the septum needle support 19 is in a retracted position as illustrated in FIGS. 6a, 6d, 7a, and 8a, the blocking finger 26 blocks the septum needle support in the retracted position by pressing against at least one of the flange sections 20. A spring 23 that may for instance be in the form of a conical coil spring, presses against a rear side of the septum needle support with a spring force configured to move the septum needle support towards the drug container and through the sealing member 27 (sterile barrier) and the septum 6c. Other forms of springs could be provided within the scope of the invention. The blocking finger 26 may be moved out of engagement with the septum needle support, for instance by being moved in a gap between the flange sections 20, such that the spring 23 pushes the septum needle support towards the sealing member 27 and septum 6c such that the septum needle 18 pierces through the sealing member and the septum.

The blocking organ 24 may, in an advantageous embodiment, comprise a rotatable support ring 25 from which the blocking finger 26 protrudes. The rotatable support ring 25 is for instance mounted around a shroud forming a cavity in which the container cap with septum 6c is inserted.

The blocking organ may be actuated to release the septum needle support allowing it to travel from the retracted to the extended position by rotation of the blocking organ 24.

In an advantageous embodiment, the movement of the blocking finger 26 and release thereof from the septum needle support 19 may be performed by actuation of the pump engine 28 of the pumping system 8. The subcutaneous delivery system 13 may also be actuated simultaneously by the initial rotation of the rotor 32 of the pump engine 28.

In the present invention, the subcutaneous delivery system may comprise a configuration similar to the delivery system described in WO 2015015379 which is incorporated herein by reference. In such configuration, the rotor 32 of the pump engine 28 comprises an actuation disc 34 coupled to the pump shaft 36, the actuation disc comprising an indent 35 that engages the tip of a lever arm 65 connected to a support ring 66 of an actuation lever 64. As best seen in reference to FIGS. 5a to 6c and FIGS. 4b and 4c, the support ring 66 of the actuation lever 64 is rotatably mounted around the shroud forming the cavity receiving the container cap, whereas the lever arm 65 extends up to a tip that is configured to catch in the indent 35 of the actuation disc 34 when the rotor 32 is rotated by the pump drive 52 of the drive unit 4.

As can be seen in FIGS. 5a and 6a, an initial position before first use of the drug delivery device is shown where the tip of the lever arm 65 rests against the outer peripheral surface of the actuation disc 34. When the pumping operation is started upon actuation of the drug delivery device, the actuation disc 34 turns (in the illustration in an anti-clockwise direction) such that the tip of the lever arm 65 engages in an indent 35 as best seen in FIG. 5b. Subsequently the continued rotation of the rotor causes the actuation lever 64 to pivot (in the illustration in a clockwise manner as shown in FIGS. 5c and 5d and 6b) until a fully actuated position shown in FIG. 5e where the injection needle 15 is fully extended. The actuation lever 64 is also coupled with a pin, protrusion or other organ (not visible in the illustrations) to the support ring 25 of the blocking organ 24 and causes it to rotate (in a clockwise manner illustrated in FIGS. 5b to 5d) such that the blocking finger 26 thereof disengages the septum needle support 19.

Thus, in the above described advantageous embodiment, the actuation of the pump drive automatically and simultaneously actuates both the subcutaneous delivery system 13 and container fully connection system 17 for administration of a drug. This simultaneous actuation upon start of the pumping system has the advantage of ensuring hermetic containment of the drug within the container until administration of the drug to the patient, thus improving sterility and shelf life duration.

As best seen in FIGS. 7a and 3c, a sealing member 27 may be provided to cover a central orifice in front of the retracted septum needle, prior to the septum needle 18 piercing through the container septum.

An orifice 68 in the casing 9 through which the injection needle 15 extends (see FIGS. 9a, 9b) may also comprise a sealing member that is pierced during actuation of the injection needle.

At the end of the injection cycle, the rotor 32 of the pump engine 28 may be reversed in order to pivot the actuation lever 64 and lever arm 65 in the opposite direction to move the needle support 16 back upwards, thus retracting the injection needle 15 within the casing 9. The patient may then safely remove the drug delivery device without danger of anyone being pricked by the injection needle 15.

In variants (not shown), an actuation of the container fluidic connection system may be performed by a different mechanism, for instance a manually actuated button on the housing, pressing the blocking finger 26 out of engagement with the septum needle support 19. In such configuration, a sensor may be provided to prevent actuation of the subcutaneous delivery system 13 and the pumping system 8 until the container fluidic connection system 17 has been actuated.

In embodiments comprising a pneumatic drive, the casing 9 comprises a container casing 38 having therein a container receiving cavity 75 that surrounds the drug container 6 and is connected to a portion of a pump and needle system casing 37 surrounding the septum needle outlet orifice, in a hermetic manner. The interior of the container casing 38 is fluidically connected via a fluidic channel 74 to an outlet 31 of the pump engine 28 as best illustrated in FIG. 13. The pneumatic flow system 74 is sealed from the volume within the pump and needle system casing 37 situated around the pump engine 8, within which an inlet 30 on the stator 29 of the pump engine 28 is positioned to draw air into the pump engine. The casing 9 may thus be provided with a valve inlet or a filter inlet (not shown) to allow air to be drawn into the volume surrounding the pump engine.

Advantageously, in the pneumatic drive configuration of embodiments of the invention, the pumping system 8 is actuated to generate a gas pressure within the container casing 38 that thus applies pressure on the back end 73 of the plunger 12. This configuration allows for a very compact delivery unit and therefore also of the drug delivery device 1, since very little space is required behind the plunger because there is no mechanical drive to directly push the plunger. Also, the use of a pump engine 28 as described above, per se known for pumping liquids, is particularly advantageous in the application of the pneumatic drive in view of the very compact size as well as the ability to pump gas without requiring additional valves. Moreover, the pump may be driven by an electrical motor without requiring gearing. Sterilization of the delivery unit 3 is also easy to perform as a substantially closed unit with gamma radiation, prior to assembly with the drug container 6.

Figure 15E:
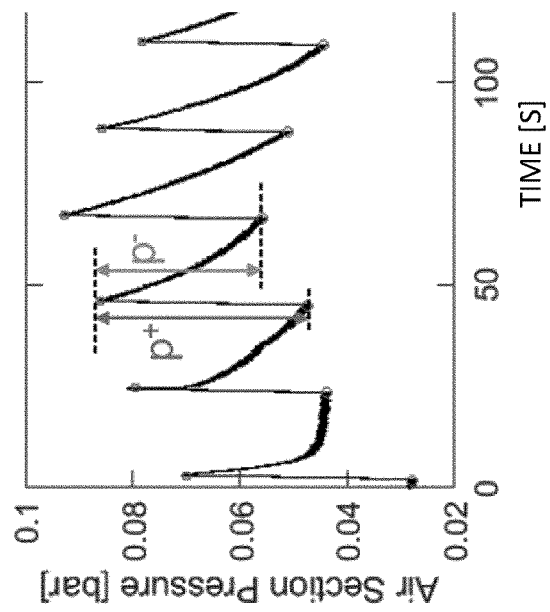
FIG. 15e is a detail portion of the plot of air pressure over time within the container holder of the drug delivery device.
Figure 15A:
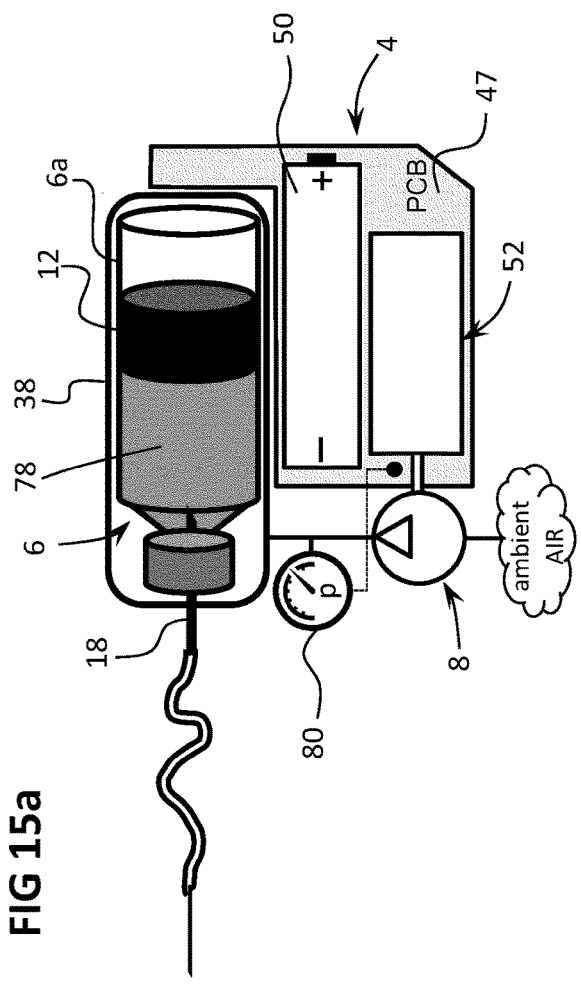
FIG. 15a is a schematic illustration of a drug container in a liquid flow pumping system of a drug delivery device according to an embodiment of the invention illustrating a pneumatic drive and a pneumatic plunger sensing system.
Figure 15B:
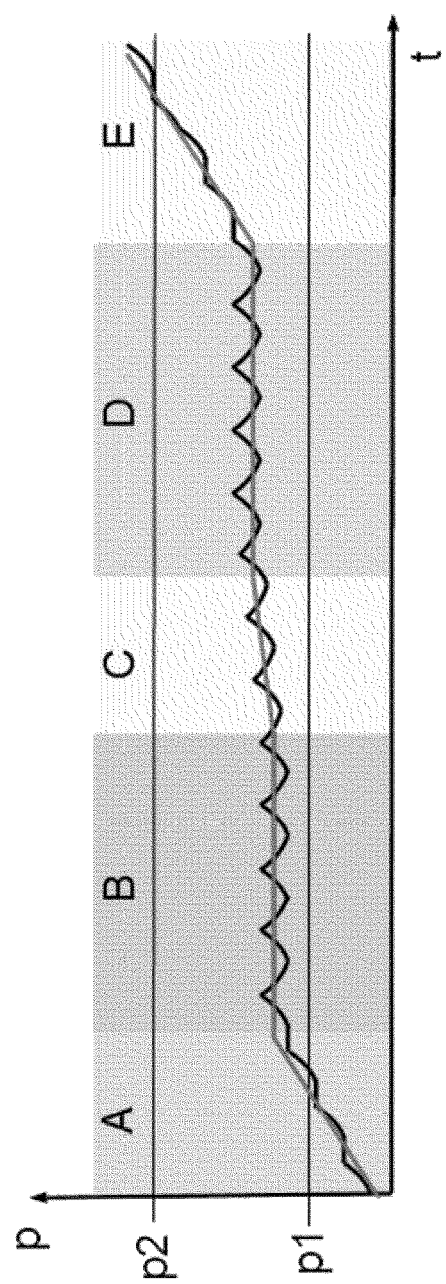
FIG. 15b is a schematic illustration of a plot of pressure as a function of time of the pneumatic plunger system according to an embodiment of the invention.

Referring to FIGS. 15a to 15d, a drug delivery device with pneumatic flow system and pneumatic drive may comprise a pressure sensor 80 to measure the pressure in the pneumatic flow system 71. The pressure in the pneumatic flow system measured over time as illustrated in FIG. 15b is indicative of the displacement of the plunger 12. Blockage of the plunger due to occlusion in the liquid flow system may be detected by an augmentation in the rate of increase of the pressure over time. Also, the end of travel of the plunger, in other words the emptying of the drug container may also be easily detected for instance by a rise in the rate of increase in pressure identified in section E of FIG. 15b.

As illustrated in FIG. 15b, if a pneumatic pump system as described above is used, the air pumping action is preferably delivered in a pulsed manner, whereby there is a pumping phase followed by an inactive phase where the pump is stopped such that there is a variation in the air pressure that gives a saw tooth characteristic as illustrated in FIGS. 15b and 15d. Each active pumping phase may be obtained by a single rotation cycle (360° rotation) of the pump engine rotor 32, or by a pre-defined plurality of rotation cycles. The inactive phase where the pump is stopped may be of a predefined duration, depending on the desired rate of drug delivery.

Evaluation of the pressure signal in the control unit 4 allows to obtain various information about the drug delivery device status, including:
  Current position of the plunger 12, thus current delivery volume→Algorithm 1
  Current speed of the plunger 12, thereby current delivery rate→Algorithm 2
  Detection of a delivery delay or a delivery standstill→Algorithm 3
  Detecting a leak in the air chamber→Algorithm 4
Examples of variants of the algorithms 1 to 4 are described below. The system information obtained from this can be processed by the control unit 4 of the pump system 8 alone or by correlating it with the feedback from other built-in sensors.

Example of Measurement Method to Determine Current Position of the Plunger 12, Thereby Current Dispensing Volume (Executed by an Algorithm 1 in the Control Unit)

Referring to FIGS. 15b, 15d and 15e, the amplitude p+, p− of the pressure fluctuations decreases towards the end of delivery. As the plunger 12 progresses, the volume behind the plunger in the air section increases, whereby, the same volume of air is added per active pump phase. The ever-decreasing ratio of the added pump volume to the air section volume results, among other things, in a reduced increase in pressure during the active pumping phase p+. The position $X_{Stopfen}$ of the plunger 12, and thus also the volume of medication already dispensed $V_{Medikament}$, correlates reciprocally with this increase in pressure, according to Boyle-Mariotte's law:

$$X_{Stopfen} = 1/P + {}^*C_0 = V_{Medikament}$$

The constant $C_0$ depends on the air volume supplied per active pump phase and the initial volume (dead volume) of the air section $C_0$ can be easily determined experimentally.

Example of Measurement Method to Determine Current Speed of the Plunger 12, Hence Current Flow Rate (Executed by an Algorithm 2 in the Control Unit)

Due to the pulsating operation of the pump, the pressure increase during the active pumping p+ phase can be compared with the pressure decrease during the inactive pumping phase p− (i.e. the pause between active pump cycles p+). This enables a statement to be made about the speed of the plug and the delivery rate.

$$p^-/p^+ C1 = x_{Stopfen} \text{ and } p^-/p^+ C2 = V_{Medikament}$$

If $p^-/p^+$ is within a cycle of pump operation and $p^-=1$, the volume of air delivered when the pressure increases corresponds to the volume of medication delivered when the pressure drops. In this state of equilibrium, the delivery rate of the drug corresponds to that of the compressed air from the pump. Deviations from the state of equilibrium are expressed in a deviation of the ratio $p^-/p^+$ from 1.

The constant $C_1$ represents the steady state plunger velocity and combines effects of friction, back pressure and pressure relative to the environment. It can be easily determined experimentally. The constant $C_2$ is calculated from the constant $C_1$ and the surface area of the plunger:

$$C_2 = C_1 * (D_{Stopfen})^2 * \pi/4.$$

Example of Measurement Method to Determine Detection of a Plunger Displacement Delay or Standstill (Executed by an Algorithm 3 in the Control Unit)

If the plunger 12 does not move or moves more slowly, the pressure in the air section behind the plunger increases. This behavior can be detected by a significant change in the ratio $p^+/p^+$ or the increase in the pressure level averaged over a longer period of time above an upper bound pressure threshold value $O_{Threshold}$ The stopping/slowing down of the plunger can have various causes:
  The delivery process is coming to an end, whereby the plunger 12 has reached the front end of the cartridge and the injection is finished;
  The delivery process is not completed, in which case the infusion needle is blocked (occlusion) or the plunger 12 is stuck, e.g. due to insufficient lubrication. In that case, issuing an alarm would be appropriate;

Example of Measurement Method to Determine Detection of a Leak in the Air Section of the Delivery Unit (Executed by an Algorithm 4 in the Control Unit)

If the pump cannot build up any or only a low pressure in the air filled section, this is most likely due to a leak. This can be detected by comparing the pressure level averaged over a certain period of time, for instance from 10 to 60 seconds, with a lower bound pressure threshold value $L_{Threshold}$.

A large amount of information can be obtained by using a single sensor which allows the system to be better monitored and made more secure. Excessive pressure, which could cause the cartridge to burst or be damaged, may be detected at an early stage.

Pressure sensors are very economical and easy to integrate. An advantage of this pneumatic plunger position sensing system is thus the very low cost and easy integration, and it is well-adapted in particular for a single injection cycle where control of the average flow rate, for instance as illustrated in FIG. 15c, is required and the end position of the plunger in the container should be determined. In such circumstances the accurate verification of the position of the plunger is not required. In such circumstances a very precise verification of the position of the plunger is not required, and for instance a positional measurement accuracy of plus or minus 10% to 20% is sufficient to detect end of delivery, occlusion, blockage, leakage, and the average rate of delivery required for the treatment. Although the accuracy of the pneumatic plunger position sensing system is lower than that of other sensing systems such as optical systems, certain treatment applications may advantageously benefit from the implementation of the pneumatic plunger position sensing system according to embodiments of this invention.

The plunger position may also be determined by other sensing means, and in another embodiment, the plunger sensing system 70 comprises an optical sensor 71 mounted on a rear end of the container facing an end 73 of the plunger 12. The container casing portion 38 of the casing 9 comprises a sensor window 43 or a sensor prism 43' mounted at an end portion 42 of the container casing 38 facing the plunger 12.

The optical sensor 71 may be positioned on an outside surface of the sensor window 43 or sensor prism 43' which is made of a transparent material for the optical signals of the optical sensor 71. The optical sensor system may advantageously comprise a transmitter 71a and a receiver 71b measuring a distance of the sensor window to the back end 73 of the plunger via a time of flight (TOF) measurement. Advantageously, such time-of-flight optical sensors are particularly economical and easy to implement. In order to obtain a practical measurement value, the window 43 may be positioned on a raised plunger end portion 42 to have a certain minimum distance from 3 mm up to 30 mm, for instance from between 5 and 20 millimeters, in the initial position of the plunger 12 when the container is full so that the plunger initial position can be more easily detected by an optical time of flight measurement.

The optical sensors 71 may be mounted on a circuit substrate 72 that projects laterally out of the drive unit 4 as schematically illustrated in FIGS. 11a, 11b and 12a, 12b. In a variant illustrated in FIGS. 12a, 12b, the optical sensor may be positioned so that the light is directed orthogonally to the direction of travel of the plunger, the light being reflected via a prism 43' with an internal reflecting surface for total internal reflection as per se known in the field of optics. The prism also has the effect of increasing the initial travel of the transmitted and reflected light so that a meaningful measurement of the initial position of the plunger when the container is full may be performed.

As the plunger moves towards the container empty position the accuracy of the time-of-flight measurement increases and thus a greater precision may be obtained as the containers reaching the empty position.

The optical sensor may be used with a pneumatic drive as previously described, however may also be used in drug delivery systems with other pumping technology for instance using a pump engine that directly draws fluid from the drug container and causes a displacement of the plunger 12 by suction (reduced pressure) within the container.

The plunger sensing system 70 with an optical sensor 71 based on a transparent window at a back end of a container casing 38 is thus particularly cost effective and easy to deploy in a very compact arrangement.

Referring to FIGS. 16a to 16e, another embodiment of a drug delivery device 1 is shown with a different arrangement of the housing 2. In this embodiment, instead of providing a container casing 38 extending the full length of the container 6, a cap 44 is provided forming a plunger end portion 42 of the container casing, that is configured to close a container receiving cavity 75 within the housing 2. A sealing ring 41 may be provided between the cap end cavity wall to hermetically close the container 6 within the housing 2. An optical sensor 71 of the plunger sensing system 70 may be incorporated within the cap 44, also positioned on a transparent sensor window 43. The optical sensors 71 may be mounted on the circuit substrate 72 that is electrically interconnected to contacts 45 projecting an outer surface of the cap for electrical connection with complementary contacts 45 on the housing 2. In this embodiment, the container 6 may thus be mounted within the housing after assembly of the drive unit 4 and delivery unit 3, for instance for allowing insertion of the container 6 by a patient or a healthcare practitioner, as opposed to a factory installation.

Figure 17B:
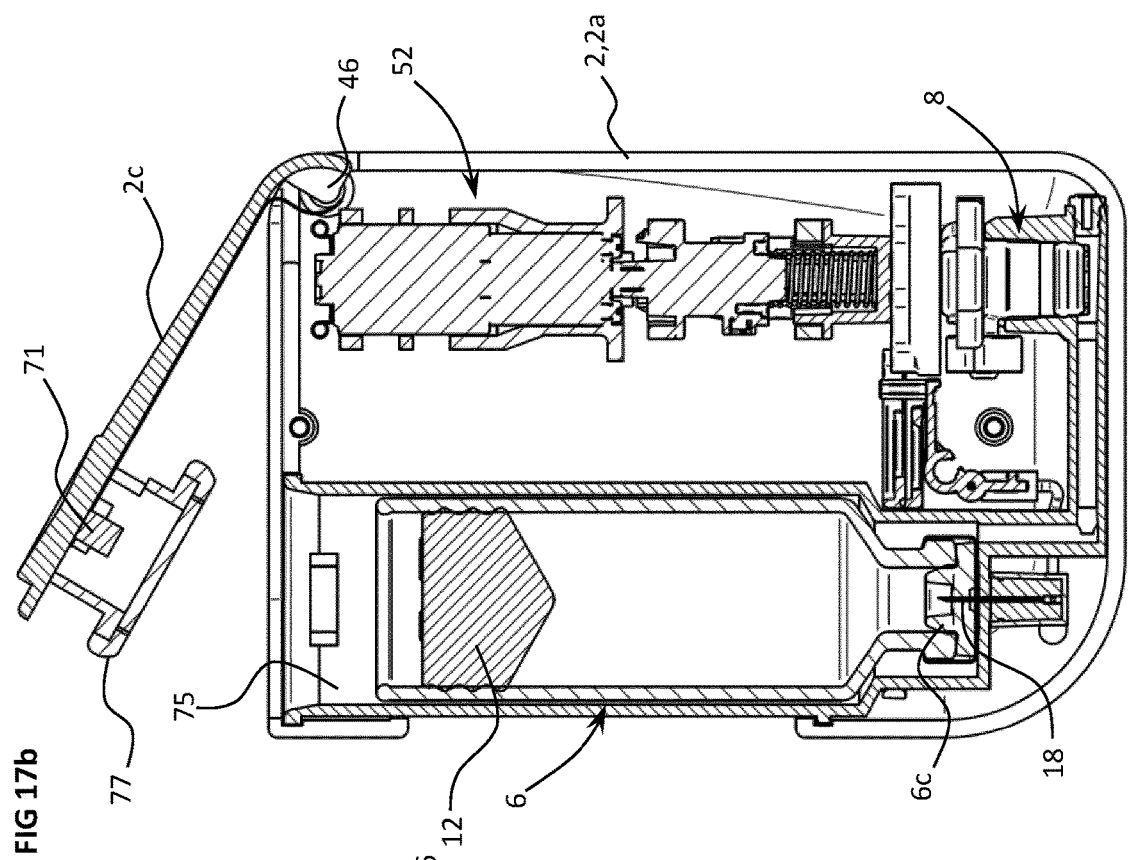
FIG. 17b is a view similar to FIG. 17a showing the components in cross section plan view.
Figure 17A:
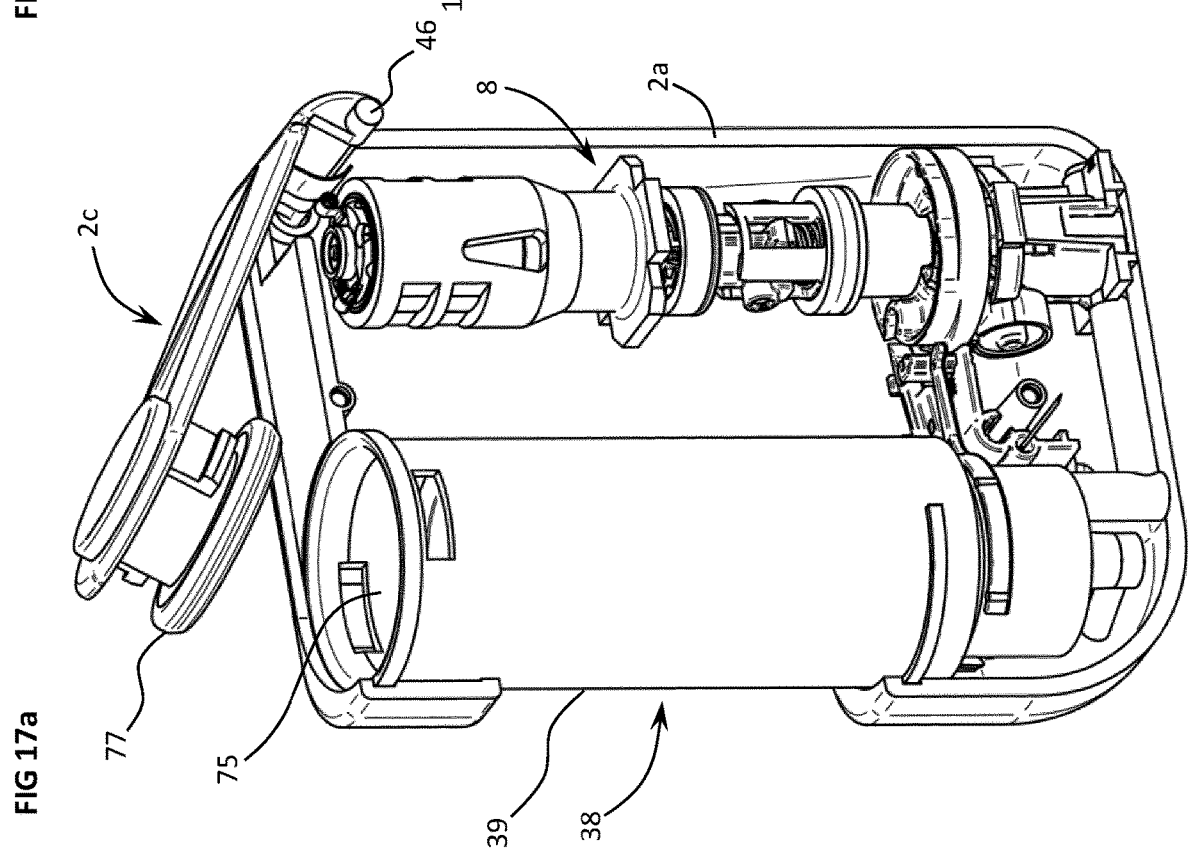
FIG. 17a is a perspective partial cross-sectional view with certain components removed of a drug delivery device according to yet another embodiment of the invention.

Referring to FIGS. 17a and 17b yet another embodiment of a drug delivery device is disclosed which also allows, similar to the embodiment of FIGS. 16a to 16d, insertion of a drug container 6 by a healthcare practitioner or user after assembly of the housing, drive unit and delivery unit in the factory. In this embodiment, the rear open end of the container casing 38 is closed by a lid 2c hingeably coupled via a hinge coupling 46 to the base 2a of the housing 2, and comprising a container sealing ring 77 that inserts and hermetically seals the rear open end of the container casing portion 38 once the container is inserted therein. It may be noted that in the figures of 17a and 17b portions of the drive unit are not shown to increase clarity of the illustration of the other parts.

Referring now to FIGS. 18a to 18d, the drug delivery device according to embodiments of the invention advantageously includes an on-body sensing system 5 electrically connected to an electronic control system 47 of the drive unit 4. The on-body sensing system 5 is based on a capacitive measurement that detects the presence of a body tissue in proximity to the capacitive sensor. Capacitive sensors for measurement the proximity of a medical device on the skin of a sensor are per se known, however conventional sensors are either not particularly reliable or are costly to integrate in a drug delivery device. In the present invention, the on-body sensing system 5 comprises an electrode 56 comprising a metal layer that is directly formed on an inside surface of the contact wall 81 of the housing, an outer surface of the skin contact wall 81 of the housing configured to be placed against the patient's skin.

The electrode 56 may advantageously be formed by deposition of a metal layer on the inside surface of the housing cover 56, for instance a plating process. The plating process may be a galvanic plating processing, but other metal deposition techniques for directly forming a metalized layer on the inside surface of the skin contact wall 81 may be utilized within the scope of the present invention. The housing may be made of a thermoplastic or thermosetting polymer and is thus an insulating material. The electrode 56 may be connected to the electronic control system 47 of the drive unit 4 via interconnection terminals 61.

The interconnection terminals 61 may be connected to the circuit board 48 of the electronic control system 47 at a circuit board connection end 62, for instance by soldering to circuit traces on the circuit board, and extend to electrode connection ends 63 contacting the metal electrode layer 56. The electrode connection ends 63 may be elastically supported, for instance by being provided at the end of a spring beam configured to press against the metal layer of the electrode 56 when the drive unit 4 is assembled within the housing 2.

Electronic components such as a microprocessor 49 of the electronic control system 47 may be connected to the electrodes to measure the capacitance value, and variations in the capacitance value, for detecting when the drug delivery device is placed against a patient's skin.

Activation of the drug delivery device may be configured in the electronic control system 47 to be possible only when the on-body sensing system detects correct position of the drug delivery device on a patient's skin.

In a first embodiment, the on-body sensing system comprises a sensor electrode implemented as a single electrode where the capacitance between the electrode and reference potential is measured.

In a second embodiment, the sensor electrodes may also be implemented as pair of electrodes 56a, 56b where the capacitance between them is measured. This has the advantage of reducing false detection due to external factors influencing the capacitance measurement such as moisture (sweat) at the contact interface, which can be rejected by the measurement system.

An advantage of the metal layer on an inner surface of the housing 2 is also the large surface area that the electrode may cover for reliable reading of a changing capacitance value in view of the large capacitive coupling with the patient's skin.

In a variant, the on-body sensing system may further comprise a conductive shield frame 57 that surrounds the electrode, providing some shielding against disturbances from external fields. The shielding may also be connected to the circuit board 48 of the electronic control system with similar contacts to those described above for connecting to the electrode layer. Instead of a metal layer directly deposited on the inner surface of the housing wall that mounts against the patient's skin, the electrode may also comprise a stamped sheet metal or thin foil of conductive material that is bonded or fixed directly against an inner surface of the housing in lieu of the deposited metal layer. The conductive foil may be bonded, for instance by adhesive or welding, against the inner surface of the housing wall 81 in order to form a stable electrode.

Figure 19A:
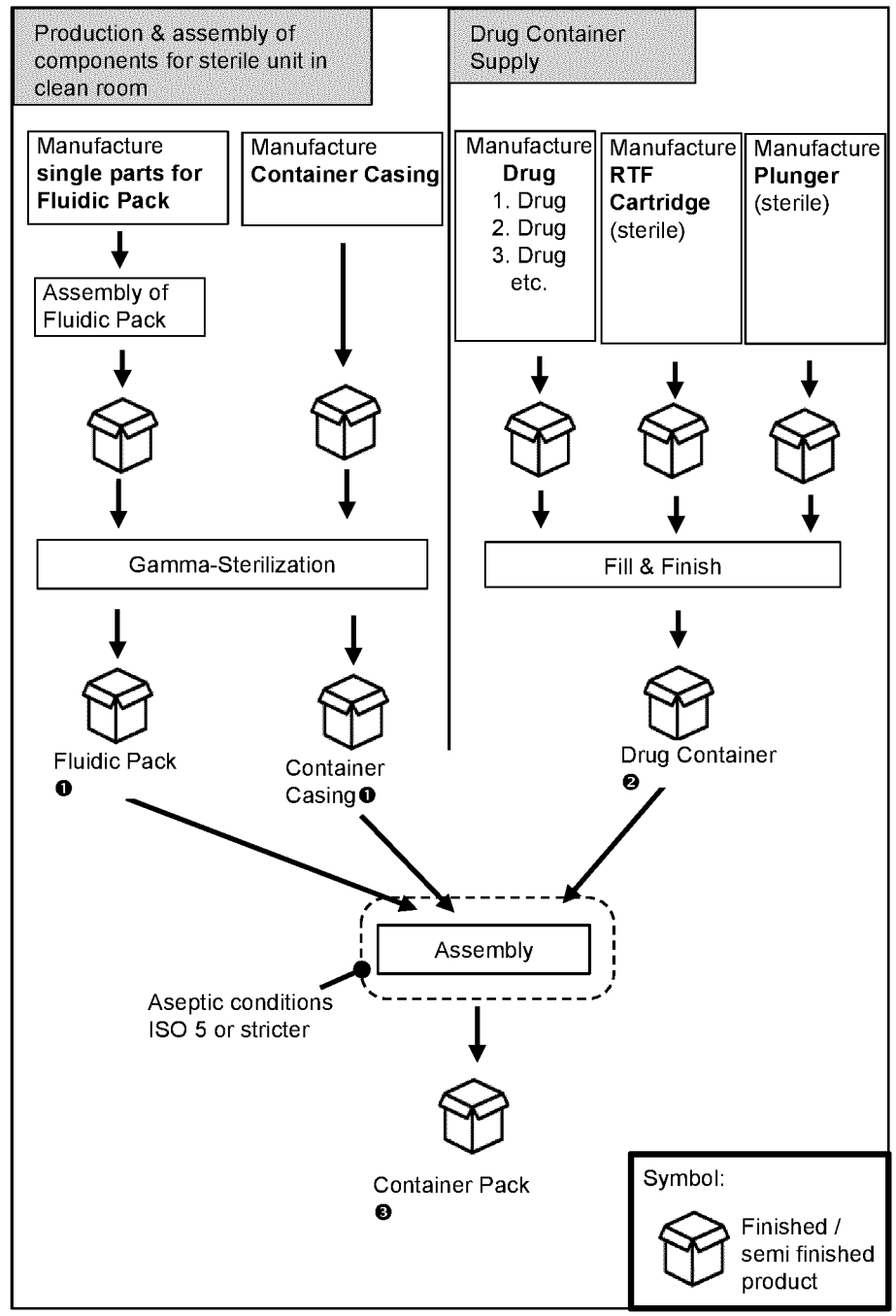
FIG. 19a to 19d are schematic representations of various embodiments of assembly and sterilization steps of a drug delivery device according to various embodiments of this invention.

Referring to FIGS. 19a to 19d, an advantageous method of assembly of a drug delivery device according to embodiments of the invention is described. Referring first to FIG. 19a, production of components of a drug delivery device that must be sterilized in a highly reliable manner is disclosed. As indicated in the illustration, the single parts for a fluidic pack are manufactured and assembled, the fluidic pack corresponding to the liquid flow and pumping system 7, 8 in the casing 9 of the above-described embodiments. The container cap illustrated in FIG. 19a corresponds to the container casing 38 and is assembled to the other casing parts once the drug container 6 has been inserted therein. The drug container components are manufactured separately and the drug container is assembled in the container cap to the fluidic pack under aseptic conditions (according to ISO standard 5 in the current example). Both container cap and fluidic pack, in other words the liquid flow system 7, pumping system 8 and casing 9, may be sterilized with gamma sterilization, which is very reliable for killing all pathogens. Other sterilization methods may be employed within the scope of the invention, including chemical and heat sterilization methods, including NO2 (nitrogen dioxide), VHP (vaporized hydrogen peroxide), ETO (ethylene oxide) and steam sterilization methods. The container pack formed from the assembly of these components thus corresponds to the delivery unit 3 which contains all the components requiring a very high degree of sterilization.

As been noted in relation to the previously described embodiments, all outlets of the delivery unit 3 are provided with seals, in particular a sealing membrane 27 covering the container fluidic connection system 17, the seal ring 41 between the container casing 38 and pump and needle casing 37, and the seal 79 covering the interface between the pumping system rotor and the drive coupling interface 33. Sealing membrane 79 may completely cover the drive coupling interface 33 as illustrated in FIG. 14c or may cover only the gap between the rotor and the stator. The sealing membrane 79 may be bonded or welded across the interface forming hermetic seal, and may for instance be frangible such that the seal ruptures or breaks when the drive unit is assembled to the delivery unit and is actuated upon use of the device. Thus the delivery unit is maintained sterile and with a long shelf life until use of the drug delivery device.

The production of the fluidic pack, container cap and drug container may occur in a single manufacturing facility and assembled in the same manufacturing facility as illustrated in FIG. 19a.

Figure 19B:
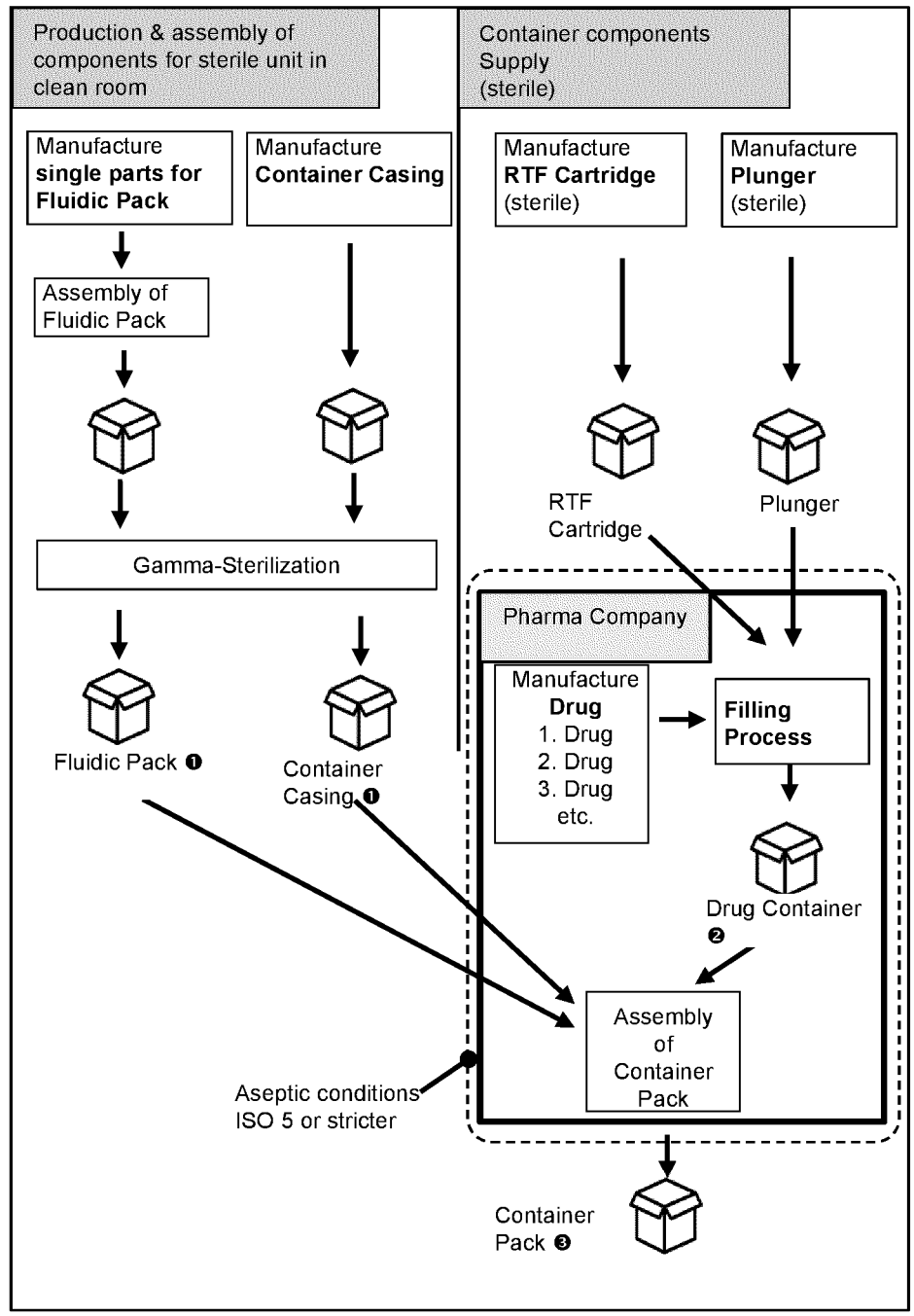

In a variant, as depicted in FIG. 19b, the fluidic cap and container cap may be manufactured in a first manufacturing facility and sterilized, preferably using gamma sterilization as in the method according to FIG. 19a, and subsequently supplied to a second facility in which the drug container is manufactured and filled, for instance in a pharmaceutical manufacturing company. As mentioned above, other sterilization methods may be employed within the scope of the invention, including chemical and heat sterilization methods (e.g. NO2, VHP, ETO, and steam sterilization methods). The assembly of the drug container and fluidic pack and container cap to form the delivery unit 3 may thus be formed within the second manufacturing site that produces the container pack.

Figure 19C:
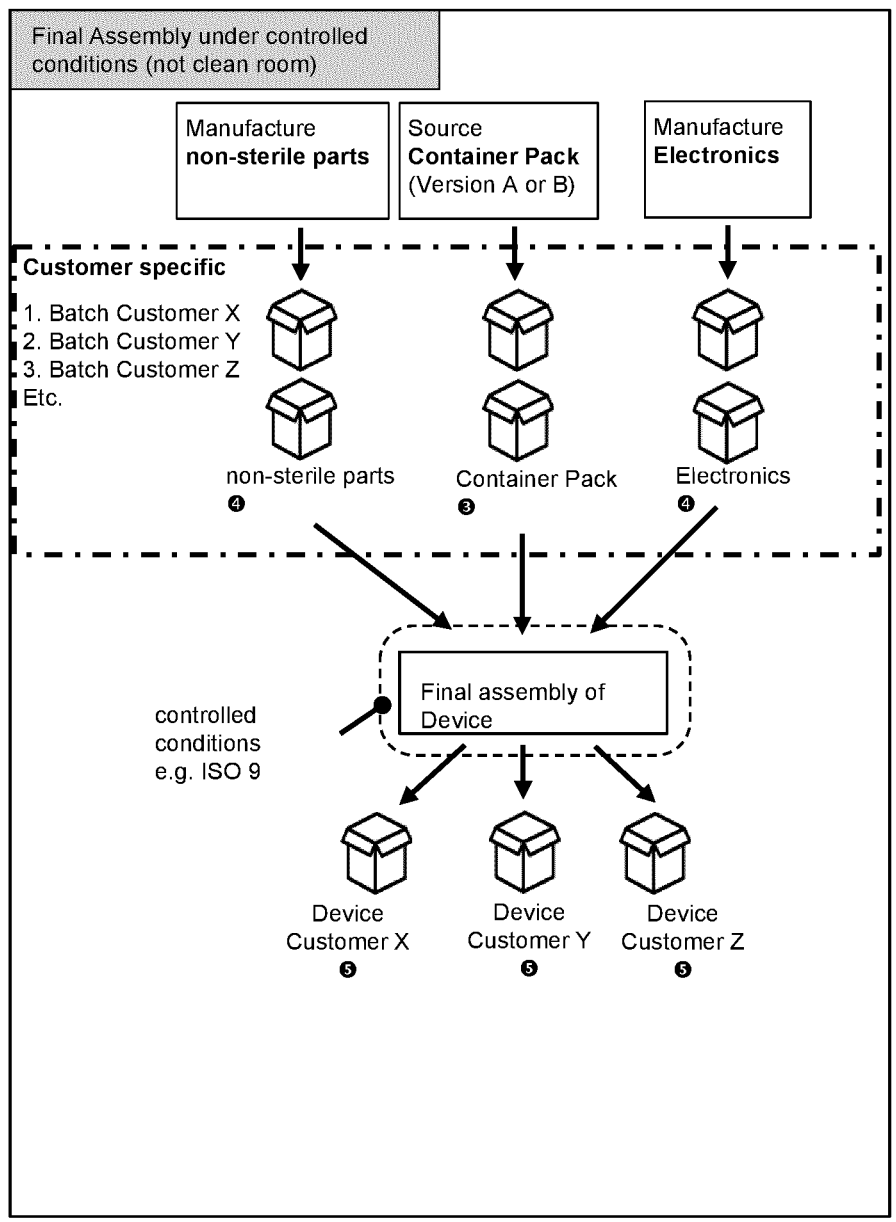
Figure 19D:
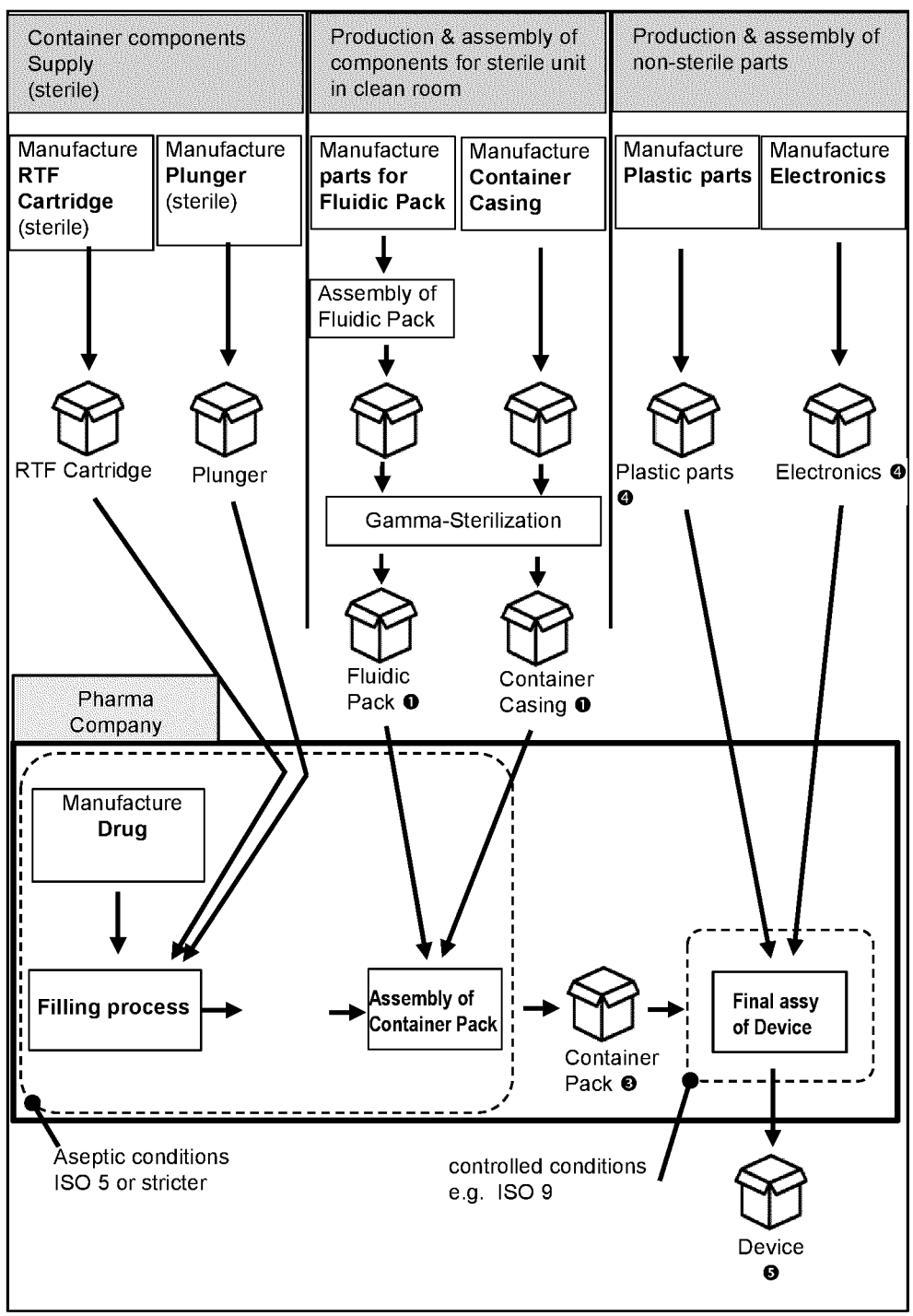

As illustrated in FIGS. 19c and FIG. 19d, the sterile container pack, representing the delivery unit 3 in embodiments herein, may then be assembled to the electronics, representing the drive unit 4 in embodiments herein, and optionally other non-sterile parts for a final assembly of the drug delivery device under controlled conditions such as ISO 9 standards.

As illustrated in FIG. 19d, various configurations of the manufacturing and assembly at different sites may be performed. For instance the drug container components may be supplied to the drug manufacturer which performs the filling process, and the fluidic pack and container cap supplied to the pharmaceutical company in a second site for assembly of the container to the fluidic pack and container cap to form the cartridge pack (i.e. corresponding to the delivery unit 3 for the embodiments described herein). The cartridge pack may then be assembled also within the site of the pharma company to the electronic parts (i.e. corresponding to the drive unit 4 for the embodiments described herein) and other parts to the cartridge pack to form the drug delivery device.

Advantageously, the configuration of the delivery unit with a casing 9 housing the liquid flow system 7 and pumping system 8 may be sterilized with gamma sterilization and then assembled to a drug container 6 to form a sealed sterile delivery unit that may then be assembled to non-sterile parts such as the electronics of the drive unit 4 and the housing parts 2. This assembly process provides for an efficient manufacturing process guaranteeing also the sterility and the safety of the drug delivery device where it is needed.

LIST OF FEATURES

Drug 78
Drug delivery device 1
Housing 2
Base 2a
Cover 2b
Skin contact wall 81
Needle orifice 10
Adhesive layer
Protective film 11
Lid 2c
Container sealing ring 77
Hinge coupling 46
Delivery unit 3
Drug container 6
Barrel portion 6a
Neck portion 6b
Septum 6c
Plunger 12
Plunger back end 73
Liquid flow system 7
Subcutaneous delivery system 13
Conduit 14
Injection needle 15
Needle support (slidable) 16
Housing slide 67
Container fluidic connection system 17
Septum needle 18
Septum needle support 19
Flange sections 20
Gap/cavity (for blocking finger release) 21
Guides 22
Spring 23
Conical spring
Blocking organ 24
Support ring (rotatable) 25
Blocking finger 26
Sealing membrane 27
Actuation lever 64
Support ring 66
Lever arm 65
Pumping system 8
Pump engine 28
Stator 29
Fluid inlet 30
Fluid outlet 31
Rotor 32
Drive coupling interface 33
Actuation disc 34
Indent 35
Pump shaft 36
Seals
Pneumatic flow system 74
Casing 9
pump and needle system casing 37
needle outlet orifice 68
container casing 38
container receiving cavity 75
tubular portion 39
septum end 40
sealing ring 41
plunger end portion 42
sensor window 43
sensor prism 43'
cap 44
electrical contact interface 45
Control unit or Drive unit 4
Electronic control system 47
Circuit board 48
Microprocessor 49
Wireless connection module
Power source (battery) 50
Pump drive 52
Motor 53
Coupling interface 54
Spring 69
User interface 55
Plunger sensing system 70
Circuit substrate 72
Optical sensor 71
Transmitter 71
Receiver 71b
Prism 43', window 43
Electrical contact interface 45
On-body sensing system 5
Electrode 56
Metallization layer
Shield 57
Processing circuit 58
Circuit board 59
Microprocessor 60
Interconnection terminals 61
Circuit board connection end 62
Electrode connection end 63
Spring beam

The invention claimed is:

1. A drug delivery device, comprising a delivery unit including a drug container for holding a liquid drug, a liquid flow system, a pumping system, and a casing, the casing enclosing the drug container, the pumping system and at least a part of the liquid flow system, the drug container comprising a barrel portion and a plunger slidably mounted within the barrel portion and sealing the liquid drug within the container at one end of the barrel portion, the liquid flow system connected fluidically to the drug container during delivery of the liquid drug, characterized in that the drug container is contained in a hermetic manner within a container receiving cavity of a container casing portion of the casing and the container receiving cavity is fluidically interconnected to a fluid outlet of the pumping system in a gas tight manner, the pumping system comprising a fluid inlet connected to environmental air, the pumping system configured to pump environmental air drawn in through the fluid inlet into the container receiving cavity generating a gas pressure within the container casing portion thus applying pressure on a back end of the plunger for delivery of the liquid drug.

2. The drug delivery device according to claim 1, wherein the pumping system comprises a pump engine including:
   a stator,
   a rotor rotatably and axially slidably mounted at least partially in the stator, the rotor comprising
   a first axial extension having a first diameter and a second axial extension having a second diameter greater than the first diameter,
   a first valve formed by a first valve seal mounted on the stator around the first axial extension, in conjunction with a first channel in the rotor that is configured to allow fluidic communication across the first valve seal when the first valve is in an open position, and
   a second valve formed by a second valve seal mounted on the stator around the second axial extension, in conjunction with a second channel in a rotor that is configured to allow fluidic communication across the second valve seal when the second valve is in an open position.

3. The drug delivery device according to claim 1, wherein the drug container is a drug cartridge and comprises a septum at one end.

4. The drug delivery device according to claim 3, comprising a container fluidic connection system including a septum needle mounted on a movable septum needle support, a spring pressing the septum needle support towards the septum of the drug container, and a blocking organ movable from a blocking position in which the septum needle support is held in a retracted position where the septum needle is not in contact with the septum, to an actuated position in which the septum needle support is released and allowed to travel towards the drug container septum such that the septum needle pierces through the septum under a force of the spring.

5. The drug delivery device according to claim 4, wherein the blocking organ comprises a rotatable support ring and a blocking finger extending from the support ring and rotatably movable with the support ring from a position in which the blocking finger engages the septum needle support and maintains it in the retracted position, to an actuated position in which the blocking finger disengages the septum needle support to allow it to travel to an actuator position where the septum needle pierces through the septum.

6. The drug delivery device according to claim 4, wherein the blocking organ is moved from a blocking position to an actuated position by an actuation mechanism comprising a rotary actuation wheel and an actuation lever, wherein the actuation wheel is directly coupled or integrally formed with a rotor of a pump engine of the pumping system.

7. The drug delivery device according to claim 1 comprising an injection delivery system including an injection needle and an injection needle actuation mechanism configured to move the injection needle from a retracted position within a housing of the drug delivery device to an extended delivery position where the injection needle projects through a base wall of the housing.

8. The drug delivery device according to claim 7, wherein the injection needle actuation mechanism includes a rotary actuation wheel and an actuation lever, wherein the actuation wheel is directly coupled or integrally formed with a rotor of a pump engine of the pumping system, the actuation lever coupled to a slidable injection needle support on which the injection needle is mounted.

9. The drug delivery device according to claim 8, wherein the actuation lever comprises a rotatable support ring and a lever arm extending from the rotatable support ring, the lever arm configured to engage an indent in an actuation disc upon initial actuation of the drug delivery device.

10. The drug delivery device according to claim 9, wherein the support ring is mounted around a shroud portion of the casing surrounding a cavity receiving the septum end of the drug container therein.

11. The drug delivery device according to claim 1, further including a drive unit comprising an electronic control system, a power source, and a pump drive, wherein the pump drive comprises a rotary electrical motor and a coupling interface coupled to an output shaft of the rotary electrical motor, the coupling interface coupling to a drive coupling interface of the pumping system of the delivery unit, the pump drive providing torque to a rotor of the pumping system.

12. The drug delivery device according to claim 1, comprising an electronic control system and a plunger sensing system including an optical sensor comprising a transmitter and a receiver, the transmitter configured for transmitting an optical signal to the back end of the plunger and the receiver configured to receive the optical signal reflected off the back end of the plunger, the plunger sensing system connected to the electronic control system configured to measure a time of flight of the optical signal from the transmitter to the receiver and to determine therefrom a position of the plunger within the cylinder portion of the drug container.

13. The drug delivery device according to claim 1, comprising a housing, a control unit mounted within the housing, the control unit comprising an on-body sensing system including an electrode connected to an electronic control system of the control unit for measuring a capacitance value configured to detect whether the drug delivery device is positioned against a patient's skin, a skin contact wall of the housing having an inner side facing an inside of the housing in which the delivery unit and the control unit are mounted, and an outer mounting side facing the outside of the housing and intended to be placed against the skin of a patient, wherein the electrode comprises a layer of metal mounted directly against the inner side of the skin contact wall.

14. The drug delivery device according to claim 1, wherein the drug delivery device further comprises a pressure sensor fluidically coupled to the container casing portion for measuring a pressure within the container casing portion, the pressure sensor connected to an electronic control system configured to measure a pressure detected by the pressure sensor over time and to determine from the pressure measurement over time a position of the plunger over time, including a stop in movement of the plunger either due to occlusion in the drug delivery flow system or an end of travel of the plunger within the container corresponding to a container empty position.

15. The drug delivery device according to claim 1, comprising a housing within which the delivery unit is assembled, the housing comprising a skin contact wall for mounting against a patient's skin, the skin contact wall comprising an adhesive layer with a protective film.

* * * * *